(12) United States Patent
Burak et al.

(10) Patent No.: US 11,191,854 B2
(45) Date of Patent: *Dec. 7, 2021

(54) PHARMACOKINETIC ENHANCEMENTS OF BIFUNCTIONAL CHELATES AND USES THEREOF

(71) Applicant: Centre for Probe Development and Commercialization, Hamilton (CA)

(72) Inventors: Eric Steven Burak, Cambridge (CA); Stuart James Mahoney, Brantford (CA); Ryan Wayne Simms, Toronto (CA); John Fitzmaurice Valliant, Ancaster (CA); Alla Darwish, Kitchener (CA)

(73) Assignee: Centre for Probe Development and Commercialization, Hamilton (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/971,963

(22) Filed: May 4, 2018

(65) Prior Publication Data

US 2019/0030194 A1    Jan. 31, 2019

Related U.S. Application Data

(60) Provisional application No. 62/502,260, filed on May 5, 2017.

(51) Int. Cl.
| | | |
|---|---|---|
| *A61K 51/00* | (2006.01) | |
| *A61M 36/14* | (2006.01) | |
| *A61K 51/04* | (2006.01) | |
| *C07D 257/02* | (2006.01) | |
| *C07F 5/00* | (2006.01) | |

(52) U.S. Cl.
CPC ........ *A61K 51/0497* (2013.01); *C07D 257/02* (2013.01); *C07F 5/00* (2013.01)

(58) Field of Classification Search
CPC .................................................. A61K 51/0497
USPC ........................................................ 424/1.53
See application file for complete search history.

(56) References Cited

U.S. PATENT DOCUMENTS

| | | | |
|---|---|---|---|
| 4,889,931 A | 12/1989 | Rocklage et al. | |
| 5,053,503 A | 10/1991 | Dean | |
| 5,175,343 A | 12/1992 | Fritzberg et al. | |
| 5,358,704 A | 10/1994 | Desreux et al. | |
| 5,364,613 A | 11/1994 | Sieving et al. | |
| 5,565,562 A | 10/1996 | Parker et al. | |
| 5,589,595 A | 12/1996 | Sandnes et al. | |
| 6,149,890 A | 11/2000 | Uggeri et al. | |
| 6,274,713 B1 | 8/2001 | Sieving et al. | |
| 6,387,891 B2 | 5/2002 | Winchell et al. | |
| 6,991,775 B2 | 1/2006 | Koerner et al. | |
| 7,385,041 B2 | 6/2008 | Chang et al. | |
| 7,385,042 B2 | 6/2008 | Fritzberg | |
| 7,696,331 B2 | 4/2010 | Fritzberg et al. | |
| 7,777,029 B2 | 8/2010 | Grotjahn et al. | |
| 8,048,906 B2 | 11/2011 | Amedio et al. | |
| 8,409,814 B2 | 4/2013 | Vogel et al. | |
| 8,420,857 B2 | 4/2013 | Bailey et al. | |
| 8,618,042 B2 | 12/2013 | Cuervo et al. | |
| 8,759,331 B2 | 6/2014 | Daiko et al. | |
| 9,163,063 B2 | 10/2015 | Mukhopadhyay et al. | |
| 9,200,017 B2 | 12/2015 | Caravan | |
| 9,284,381 B2 | 3/2016 | Josephson et al. | |
| 10,093,741 B1* | 10/2018 | Burak ................ | C07K 16/2863 |
| 2002/0052354 A1 | 5/2002 | Platzek et al. | |
| 2004/0204561 A1 | 10/2004 | Ellison | |
| 2005/0007200 A1 | 1/2005 | Inoue et al. | |
| 2005/0064485 A1 | 3/2005 | Vogel | |
| 2006/0009504 A1 | 1/2006 | Heimbecher et al. | |
| 2006/0222595 A1 | 10/2006 | Mukherjee et al. | |
| 2006/0233704 A1 | 10/2006 | Maecke et al. | |
| 2006/0235296 A1 | 10/2006 | Mattiuzzi et al. | |
| 2007/0009442 A1 | 1/2007 | Platzek et al. | |
| 2007/0014725 A1 | 1/2007 | Platzek et al. | |
| 2007/0020183 A1 | 1/2007 | Schirmer et al. | |
| 2007/0053837 A1* | 3/2007 | Merlo ................. | A61K 49/085 424/1.69 |
| 2008/0058636 A1 | 3/2008 | Caravan et al. | |
| 2008/0299040 A1* | 12/2008 | Rivier ................. | C07K 14/655 424/1.69 |
| 2009/0053137 A1 | 2/2009 | Moore | |
| 2009/0297454 A1 | 12/2009 | Schirmer et al. | |
| 2010/0081799 A1 | 4/2010 | Knor et al. | |
| 2010/0226884 A1* | 9/2010 | Chang ................... | A61K 45/06 424/85.5 |
| 2011/0117015 A1 | 5/2011 | Rossello et al. | |
| 2011/0129425 A1 | 6/2011 | Meyer et al. | |
| 2012/0213781 A1 | 8/2012 | Hilbert | |

(Continued)

FOREIGN PATENT DOCUMENTS

| | | |
|---|---|---|
| EP | 0468634 A1 | 1/1992 |
| EP | 2397466 A1 | 12/2011 |

(Continued)

OTHER PUBLICATIONS

Tolmachev et al. J. Nucl. Med. 2012, 53, 90-97.*
Bernhard et al. Chem. Eur. J. 2012, 18, 7834-7841.*
Nolting Antibody Drug Conj. 2013, 71-100. (Year: 2013).*
Afratis et al, Scientific Reports, 7:40138, DOI: 10.1038/srep40138, Jan. 2017, pp. 1-12.
Bernhard et al. "DOTAGA-Anhydride: A Valuable Building Block for the Preparation of DOTA-Like Chelating Agents" Chem. Eur. J. 2012, 18, 7834-7841.
Ceulemans, Matthias, et al. "Gadolinium (III)-DOTA complex functionalized with BODIPY as a potential bimodal contrast agent for MRI and optical imaging." Inorganics vol. 3, No. 4, pp. 516-533, Nov. 2015.

(Continued)

*Primary Examiner* — Michael G. Hartley
*Assistant Examiner* — Sean R Donohue
(74) *Attorney, Agent, or Firm* — Goodwin Procter LLP

(57) ABSTRACT

The present invention relates to conjugates including a chelating moiety of a metal complex thereof and a therapeutic or targeting moiety, methods for their production, and uses thereof.

16 Claims, 4 Drawing Sheets

Specification includes a Sequence Listing.

(56) References Cited

U.S. PATENT DOCUMENTS

| | | |
|---|---|---|
| 2013/0309176 A1 | 11/2013 | Port et al. |
| 2013/0337564 A1 | 12/2013 | Davis et al. |
| 2014/0005100 A1 | 1/2014 | Su et al. |
| 2014/0227297 A1 | 8/2014 | Goonewardena et al. |
| 2014/0228551 A1 | 8/2014 | Tworowska et al. |
| 2014/0314670 A1 | 10/2014 | D'Addona et al. |
| 2014/0323363 A1 | 10/2014 | Perriat et al. |
| 2014/0378668 A1 | 12/2014 | Barbas, III et al. |
| 2015/0017188 A1 | 1/2015 | Eigenbrot, Jr. et al. |
| 2015/0056191 A1 | 2/2015 | Sathyanarayanan et al. |
| 2015/0202335 A1 | 7/2015 | Shen et al. |
| 2015/0258221 A1 | 9/2015 | Brioschi et al. |
| 2015/0283272 A1 | 10/2015 | Kundra et al. |
| 2017/0029516 A1 | 2/2017 | Gerstam |
| 2017/0043033 A1 | 2/2017 | Strop |

FOREIGN PATENT DOCUMENTS

| | | | |
|---|---|---|---|
| WO | WO-9211858 A1 | 7/1992 | |
| WO | WO-9325240 A2 | 12/1993 | |
| WO | WO-0038738 A1 | 7/2000 | |
| WO | WO-0151095 A2 | 7/2001 | |
| WO | WO-2004039409 A3 | 9/2004 | |
| WO | WO-2004082722 A2 | 9/2004 | |
| WO | WO-2005079803 A1 | 9/2005 | |
| WO | WO-2008091530 A2 | 7/2008 | |
| WO | WO-2008134289 A3 | 12/2008 | |
| WO | WO-200932145 A1 | 3/2009 | |
| WO | WO-2009124764 A1 | 10/2009 | |
| WO | WO-2010052243 A3 | 8/2010 | |
| WO | WO-2011005609 A3 | 5/2011 | |
| WO | WO-2011090492 A1 | 7/2011 | |
| WO | WO-2013105753 A1 | 7/2013 | |
| WO | WO-2012122420 A3 | 4/2014 | |
| WO | WO-2014180524 A1 | 11/2014 | |
| WO | WO-2015/023979 A1 | 2/2015 | |
| WO | WO-2015038968 A1 | 3/2015 | |
| WO | WO-2015055318 A1 | 4/2015 | |
| WO | WO-2015073575 A2 | 5/2015 | |
| WO | WO-2015085005 A1 | 6/2015 | |
| WO | WO-2015092310 A1 | 6/2015 | |
| WO | WO-2015132602 A1 | 9/2015 | |
| WO | WO-2015157595 A1 | 10/2015 | |
| WO | WO-2015162563 A1 | 10/2015 | |
| WO | WO-2015176056 A1 * | 11/2015 | ......... C07K 16/2803 |
| WO | WO-2016016329 A1 | 2/2016 | |
| WO | WO-2016030104 A1 | 3/2016 | |
| WO | WO-2016058704 A1 | 4/2016 | |
| WO | WO-2016046793 A3 | 6/2016 | |
| WO | WO-2016086021 A1 | 6/2016 | |
| WO | WO-2017120193 A1 * | 7/2017 | ............ A61K 47/61 |
| WO | 2017161356 A1 | 9/2017 | |
| WO | WO-2017161356 A1 | 9/2017 | |
| WO | WO-2018204869 A1 | 11/2018 | |

OTHER PUBLICATIONS

Chen, Xiaoyuan, et al. "Integrin alpha beta 3-Targeted Imaging of Lung Cancer." Neoplasia, vol. 7, No. 3, pp. 271-279.
Chang et al. "Evaluation of a Novel Hexavalent Humanized Anti-IGF-1R Antibody and Its Bivalent Parental IgG in Diverse Cancer Cell Lines" Aug. 2012 | vol. 7 | Issue 8 | e44235—pp. 1-14.
Cox J. P. L. et al. "Synthesis of C- and N-functionalised derivatives of 1,4, 7-triazacyclononane-1,4, 7-triyltriacetic acid (NOTA), 1, 4, 7, 10-tetra-azacyclododecane-1, 4, 7,10-tetralyltetra-acetic acid (DOTA), and diethylenetriaminepenta-acetic acid (DTPA): bifunctional complexin", Journal of the Chemical Society, Perkin Transactions 1, Royal Society of Chemistry, Cambridge, UK, No. 9, Jan. 1, 1990 (Jan. 1, 1990), pp. 2567-2576.
Doern et al., "Characterization of inhibitory anti-insulin-like growth factor receptor antibodies with different epitope specificity and ligand-blocking properties," J Biol Chem. 284(15):10254-67 (2009).
Evans, Helen L., et al. "A bioorthogonal 68 Ga-labelling strategy for rapid in vivo imaging." Chemical Communications vol. 50, No. 67, pp. 9557-9560, 2014.
Gualberto et al., "Development of the monoclonal antibody figitumumab, targeting the insulin-like growth factor-1 receptor, for the treatment of patients with non-small-cell lung cancer," Clin Lung Cancer. 10(4):273-80 (2009).
International Search Report and Written Opinion dated Aug. 2, 2018 in International (PCT) Application No. PCT/US2018/031228 (13 pages).
International Search Report and Written Opinion dated Oct. 30, 2018 in International (PCT) Application No. PCT/US2018/031233 (15 pages).
Leung, Kam. "III In-1, 4, 7, 10-Tetraazacyclododecanse-1, 4, 7, 10-tetraacetic acid-anti-insulin-like growth factor 1 receptor Affibody ZIGF1R: 4551." Molecular Imaging and Contrast Agent Database, Mar. 29, 2012. Retrieved from URL: www.ncbi.nlm.nih.gov/books/NBK91425<http://www.ncbi.nlm.nih.gov/books/NBK91425> on Oct. 15, 2018.
Nolting, Birte "Linker Technologies for Antibody-Drug Conjugates" Antibody Drug Conj. 2013, Methods in Molecular Biology, vol. 1045, 71-100.
Notice of Allowance dated Jun. 21, 2018 in U.S. Appl. No. 15/678,027 (6 pages).
Office Action dated Feb. 7, 2018 in U.S. Appl. No. 15/678,027 (16 pages).
Office Action dated May 31, 2018 in U.S. Appl. No. 15/678,027 (8 pages).
Rivera-Monroy et al., "Fluorescent isotope-coded affinity tag (FCAT). I: Design and synthesis," Bioorg Chem. 36(6):299-311 (2008).
Toimachev et al. "Imaging of Insulinlike Growth Factor Type 1 Receptor in Prostate Cancer Xenografts Using the Affibody Molecule 111 In-DOTA-Z1GF1R:4ss1 " J. Nucl. Med. The Journal of Nuclear Medicine, vol. 53, No. I, Jan. 2012, 90-97.
Vaidyanathan et al., "Evaluation of an anti-p185(HER2) (scFv—C(H)2—C(H)3)2 fragment following radioiodination using two different residualizing labels: SGMIB and IB-Mal-D-GEEEK," available in PMC Aug. 1, 2010, published in final edited form as:Nucl Med Biol. 36(6):671-80 (2009) (19 pages).
Vaidyanathan et al., "N epsilon-(3-[*I]Iodobenzoyl)-Lys5-N alpha-maleimido-Gly1-GEEEK ([*I]IB-Mal-D-GEEEK): a radioiodinated prosthetic group containingnegatively charged D-glutamates for labeling internalizing monoclonal antibodies," Bioconjug Chem. 17(4):1085-92 (2006).
Zhang, Yin, et al. "Molecular imaging of insulin-like growth factor 1 receptor in cancer." American journal of nuclear medicine and molecular imaging, vol. 2, No. 2, pp. 248-259, Mar. 28, 2012.
Anonymous: "A Phase 1 Study of [225Ac]-FPI-1434 Injection", ClinicalTrials.gov NCT03746431, Nov. 19, 2018, Retrieved from the Internet: URL:https://clinicaltrials.gov/ct2/show/NC_July_16<URL:https://clinicaltrials.gov/ct2/show/NC%20July%2016>, 2020.
Burak et al., "Single dose Efficacy of FPI-1434, a radioimmunoconjugate targeting human IGF-1R, in preclinical models of human cancer", European Journal of Nuclear Medicine and Molecular Imaging, vol. 45, No. Supplement 1, Oct. 1, 2018.
Forbes et al., "FPX-o1: A radioimmunoconjugate targeting human IGF-1R", Journal of Nuclear Medicine, vol. 59, No. Supplement 1, May 1, 2018.
Geoerger et al., "Anti-insulin-like growth factor 1 receptor antibody EM164 (murine AVE1642) exhibits anti-tumour activity alone and in combination with temozolomide against neuroblastoma", European Journal of Cancer, vol. 46, No. 18, pp. 3251-3262, Dec. 1, 2021.
Heskamp et al. "ImmunoSPECT and ImmunoPET of IGF-1R Expression with the Radiolabeled Antibody R1507 in a Triple-Negative Breast Cancer Model", The Journal of Nuclear Medicine, vol. 51, No. 10, pp. 1565-1572, Oct. 1, 2020.
Juergens et al., "A phase I study of [225Ac]-FPI-1434 radioimmunotherapy in patients with IGF-1R expressing solid tumors", Journal of Clinical Oncology, vol. 37, No. Supplement 15, May 1, 2019.
Simms et al., "Enhanced metabolic elimination radioactivity associated with DOTA chelates from radioimmunoconguates", Journal of Nuclear Medicine, vol. 59, No. Supplement 1, May 1, 2018.

(56) References Cited

OTHER PUBLICATIONS

Soria et al., "A dose finding, safety and pharmacokinetic study of AVE1642, an anti-insulin-like growth factor-1 receptor (IGF-1R/CD221) monoclonal antibody, administered as a single agent and in combination with docetaxel in patients with advanced solid tumours", European Journal of Cancer, vol. 49, No. 8, pp. 1799-1807, May 1, 2013.
U.S. Appl. No. 15/678,027, filed Aug. 15, 2017.
U.S. Appl. No. 15/971,980, filed May 4, 2018.

* cited by examiner

PHARMACOKINETIC ENHANCEMENTS OF BIFUNCTIONAL CHELATES AND USES THEREOF

RELATED APPLICATIONS

The present application claims priority to, and the benefit of, U.S. Provisional Patent Application No. 62/502,260 titled "PHARMACOKINETIC ENHANCEMENTS OF BIFUNCTIONAL CHELATES AND USES THEREOF" and filed on May 5, 2017, the entire contents of which are hereby incorporated by reference for all purposes.

SEQUENCE LISTING

This application contains a Sequence Listing which has been submitted electronically in ASCII format and which is incorporated by reference in its entirety. Said ASCII file is named 105251_0013_Sequence_Listing_ST25.txt, is 4,096 bytes in size and was created on Oct. 14, 2018.

BACKGROUND

Radiolabelled targeting moieties, or radioconjugates, are typically prepared by using a bifunctional chelator to append a radiolabel to a biological molecule while maintaining target affinity. Bifunctional chelates structurally may contain a chelate, a linker, and a cross-linking group or targeting moiety. By modifying the linker region of the bifunctional chelate, pharmacokinetic advantages can be obtained that can increase the excretion of radioactivity.

SUMMARY OF THE INVENTION

The present invention is directed to linkers that enhance the excretion of a chelating moiety, or a metal complex thereof, when conjugated to a therapeutic moiety, a targeting moiety, or a cross-linking group.

Accordingly, in a first aspect, the invention features a compound having the structure:

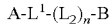
A-L$^1$-(L$_2$)$_n$-B   Formula I wherein A is chelating moiety or a metal complex thereof;
L$^1$ is optionally substituted C$_1$-C$_6$ alkyl, substituted C$_1$-C$_6$ heteroalkyl, substituted aryl or heteroaryl;
B is a therapeutic moiety, a targeting moiety, or cross-linking group,
or a pharmaceutically acceptable salt thereof;
n is 1-5;
each L$^2$, independently, has the structure:

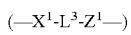
(—X$^1$-L$^3$-Z$^1$—)   Formula II wherein is X$^1$ is C=O(NR$^1$), C=S(NR$^1$), OC=O(NR$^1$), NR$^1$C=O(O), NR$^1$C=O(NR$^1$), —CH$_2$PhC=O(NR$^1$), —CH$_2$Ph(NH)C=S(NR$^1$) , O, NR$^1$ and R$^1$ is H or optionally substituted C$_1$-C$_6$ alkyl or optionally substituted C$_1$-C$_6$ heteroalkyl, substituted aryl or heteroaryl; L$^3$ is optionally substituted C$_1$-C$_{50}$ alkyl or optionally substituted C$_1$-C$_{50}$ heteroalkyl or C$_5$-C$_{20}$ polyethylene glycol; Z$^1$ is CH$_2$, C=O, C=S, OC=O, NR$^1$C=O, NR$^1$ and R$^1$ is a hydrogen or optionally substituted C$_1$-C$_6$ alkyl, pyrrolidine-2,5-dione.

In some embodiments, the chelating moiety is DOTA (1,4,7,10-tetraazacyclododecane-1,4,7,10-tetraacetic acid), DOTMA (1R,4R,7R,10R)-α, α', α", α'''-tetramethyl-1,4,7,10-tetraazacyclododecane-1,4,7,10-tetraacetic acid, DOTAM (1,4,7,10-tetrakis(carbamoylmethyl)-1,4,7,10-tetraazacyclododecane), DOTPA (1,4,7,10-tetraazacyclododecane-1,4,7,10-tetra propionic acid), DO3AM-acetic acid (2-(4,7,10-tris(2-amino-2-oxoethyl)-1,4,7,10-tetraazacyclododecan-1-yl)acetic acid), DOTA-GA anhydride (2,2',2"-(10-(2,6-dioxotetrahydro-2H-pyran-3-yl)-1,4,7,10-tetraazacyclododecane-1,4,7-tril)triacetic acid, DOTP (1,4,7,10-tetraazacyclododecane-1,4,7,10-tetra (methylene phosphonic acid)), DOTMP (1,4,6,10-tetraazacyclodecane-1,4,7,10-tetramethylene phosphonic acid, DOTA-4AMP (1,4,7,10-tetraazacyclododecane-1,4,7,10-tetrakis(acetamido-methylenephosphonic acid), CB-TE2A (1,4,8,11-tetraazabicyclo[6.6.2]hexadecane-4,11-diacetic acid), NOTA (1,4,7-triazacyclononane-1,4,7-triacetic acid), NOTP (1,4,7-triazacyclononane-1,4,7-tri(methylene phosphonic acid), TETPA (1,4,8,11-tetraazacyclotetradecane-1,4,8,11-tetrapropionic acid), TETA (1,4,8,11-tetraazacyclotetradecane-1,4,8,11-tetra acetic acid), HEHA (1,4,7,10,13,16-hexaazacyclohexadecane-1,4,7,10,13,16-hexaacetic acid), PEPA (1,4,7,10,13-pentaazacyclopentadecane-N,N', N",N''', N''''-pentaacetic acid), H$_4$Octapa (N,N'-bis(6-carboxy-2-pyridylmethyl)-ethylenediamine-N,N'-diacetic acid), H$_2$Dedpa (1,2-[[6-(carboxy)-pyridin-2-yl]-methylamino]ethane), H$_6$phospa (N,N'-(methylenephosphonate)-N,N'-[6-(methoxycarbonyl)pyridin-2-yl]-methyl-1,2-di-aminoethane), TTHA (triethylenetetramine-N,N,N',N",N''', N''''-hexaacetic acid), DO2P (tetraazacyclododecane dimethanephosphonic acid), HP-DO3A (hydroxypropyltetraazacyclododecanetriacetic acid), EDTA (ethylenediaminetetraacetic acid), Deferoxamine, DTPA (diethylenetriaminepentaacetic acid), DTPA-BMA (diethylenetriaminepentaacetic acid-bismethylamide), HOPO (octadentate hydroxypyridinones) or porphyrin.

The person having ordinary skill in the art will understand that the use of chelating moieties in the practice of the invention are not limited to the specific constructs disclosed herein, but rather may include other known chelating moieties.

In some embodiments, the chelating moiety has the structure:

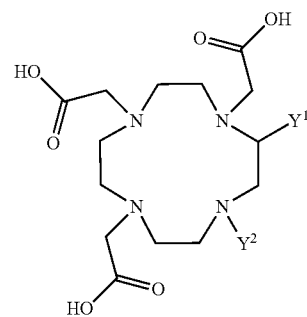

wherein Y$^1$ is —CH$_2$OCH$_2$(L$^2$)$_n$-B, C=S(L$^2$)$_n$-B, or C=S(L$^2$)$_n$-B and Y$^2$ is —CH$_2$CO$_2$H;
wherein Y$^1$ is H, Y$^2$ is L$^1$-(L$^2$)$_n$-B In some embodiments, L$^1$ has the structure:

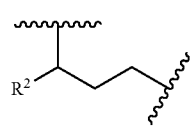

Formula III wherein R$^2$ is optionally substituted hydrogen or —CO$_2$H

In some embodiments, the metal can be selected from Bi, Pb, Y, Mn, Cr, Fe, Co, Zn Ni, Tc, In, Ga, Cu, Re, Sm, a lanthanide, or an actinide, for use as imaging or therapeutic agents. Specific examples of radionuclides suitable for complexing to a compound of formula (I) include $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pp, $^{212}$Bi, $^{213}$Bi, $^{225}$Ac, and $^{227}$Th.

In some embodiments, B is a therapeutic moiety or targeting moiety.

In some embodiments, the therapeutic moiety or targeting moiety is an antibody, an antigen-binding fragment thereof or other targeting protein such as nanobodies, affibodies, and consensus sequences from Fibronectin type III domains.

In some embodiments, the antibody, or an antigen-binding fragment thereof specifically binds insulin-like growth factor-1 receptor (IGF-1R).

In some embodiments, the cross-linking group is an amino-reactive, a methionine-reactive cross linking group, a thiol-reactive cross-linking group or a sortase-mediated coupling sequence.

In some embodiments, the amino-reactive, a methionine-reactive or thiol-reactive cross-linking group comprises an activated ester such as a hydroxysuccinimide ester, N-hydroxysulfosuccinimide, 2,3,5,6-tetrafluorophenol ester, 4-nitrophenol ester or an imidate, anhydride, thiol, disulfide, maleimide, azide, alkyne, strained alkyne, strained alkene, halogen, sulfonate, haloacetyl, amine, hydrazide, diazirine, phosphine, tetrazine, isothiocyanate, or an oxaziridine.

In some embodiments, the sortase recognition sequence may comprise of a terminal glycine-glycine-glycine (GGG) and/or LPTXG (SEQ ID NO: 1) amino acid sequence, where X is any amino acid.

The person having ordinary skill in the art will understand that the use of cross linking groups in the practice of the invention are not limited to the specific constructs disclosed herein, but rather may include other known cross linking groups.

In some embodiments, the cross-linking group is selected from the group consisting of:

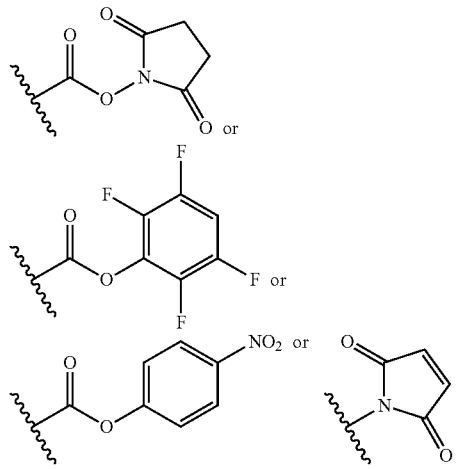

In some embodiments, $Y^1$ is H.
In some embodiments, $X^1$ is C=O(NR$^1$) and R$^1$ is H.
In some embodiments, $Z^1$ is —CH$_2$.
In some embodiments, $L^2$ has n value of 1.
In some embodiments, the compound is selected from the group consisting of:

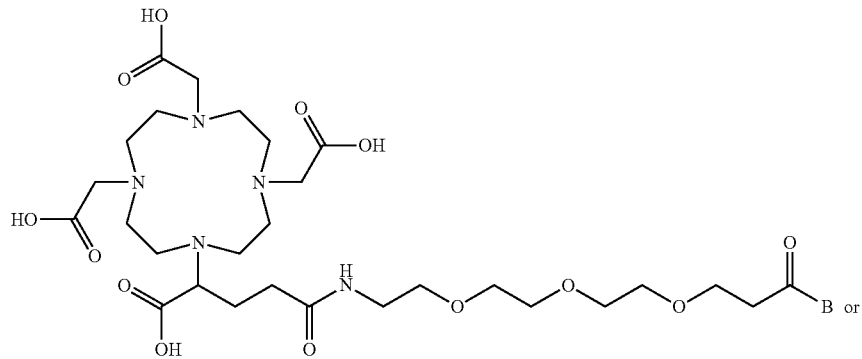

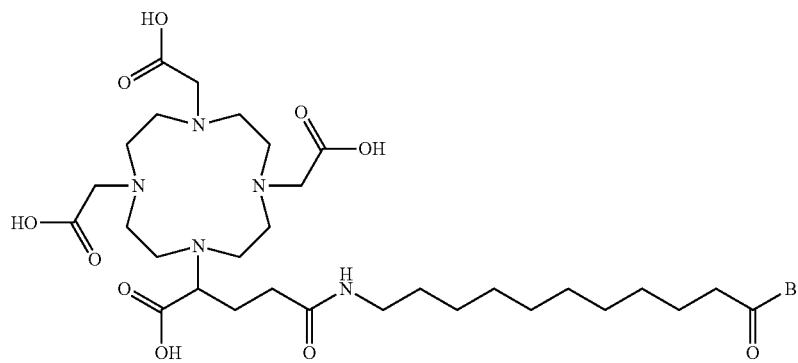

In some embodiments, the metal is a radionuclide.
In some embodiments, the radionuclide is $^{111}$In.
In some embodiments, the radionuclide is $^{68}$Ga.
In some embodiments, the radionuclide is $^{86}$Y.
In some embodiments, the metal is a beta-emitting radionuclide.
In some embodiments, the radionuclide are $^{67}$Cu, $^{177}$Lu' or $^{90}$Y
In some embodiments, the metal is an alpha-emitting radionuclide.
In some embodiments, the radionuclide is $^{225}$Ac, $^{212}$Pb, $^{227}$Th or the progeny (daughter isotopes) thereof.

In another aspect, the invention features a pharmaceutical composition including any of the foregoing compounds and a pharmaceutically acceptable excipient.

In another aspect, the invention features a method of radiation treatment planning and/or radiation treatment, the method comprising administering to a subject in need thereof any of the foregoing compounds or pharmaceutical compositions.

In another aspect, the invention features a method of detecting and/or treating cancer, the method including administering to a subject in need thereof a first dose of any of the foregoing compounds or pharmaceutical compositions in an amount effective for radiation treatment planning, followed by administering subsequent doses of any of the foregoing compounds or pharmaceutical compositions in a therapeutically effective amount.

In some embodiments, the compound or composition administered in the first dose and the compound or composition administered in the second dose are the same.

In some embodiments, the compound or composition administered in the first dose and the compound or composition administered in the second dose are different.

In some embodiments, the cancer is a solid tumor or hematologic (liquid) cancer.

In some embodiments, the solid tumor cancer is breast cancer, non-small cell lung cancer, small cell lung cancer, pancreatic cancer, head and neck cancer, prostate cancer, colorectal cancer, sarcoma, adrenocortical carcinoma, neuroendocrine cancer, Ewing's Sarcoma, multiple myeloma, or acute myeloid leukemia.

In some embodiments, the foregoing methods further include administering an antiproliferative agent, radiation sensitizer, or an immunoregulatory or immunomodulatory agent.

In some embodiments, any of the foregoing compounds or compositions thereof and an antiproliferative agent or radiation sensitizer are administered within 28 days (e.g., within 14, 7, 6, 5, 4, 3, 2, or 1 day(s)) of each other.

In some embodiments, any of the above-described compounds or compositions thereof and an immunoregulatory or immunomodulatory agent are administered within 90 days (e.g., within 80, 70, 60, 50, 40, 30, 20, 10, 5, 4, 3, 2, or 1 day(s)) of each other.

In another aspect, the invention features a method of making a radioconjugate (e.g., any of the radioconjugates described herein). The method includes the steps of (a) conjugating a bifunctional chelate to a biological molecule, (b) purifying the conjugate produced by step (a), and (c) chelating one or more radionuclides (e.g., one or more Ac-225 radionuclides) with the purified conjugate of step (b) at a temperature of less than 35° C. (e.g., 20-25° C.) to produce a radioconjugate (e.g. an actinium radioconjugate).

In some embodiments, the radioconjugate is a radioimmunoconjugate (e.g., any of the radioimmunoconjugates described herein).

In some embodiments, the pH of the reaction mixture of conjugation step (a) is less than 6.4 (e.g., 6.3, 6.2, 6.1, 6.0, 5.9, or 5.8 or less).

In some embodiments, the pH of the reaction mixture of conjugation step (c) is less than 5.5 (e.g., 5.4, 5.3, 5.2, 5.1, or 5.0 or less) or more than 7.0 (e.g., 7.1, 7.2, 7.3, 7.4, 7.5 or more).

In some embodiments, the temperature of the reaction mixture of conjugation step (c) is 20-34° C. (e.g., 21° C., 22° C., 23° C., 24° C., 25° C., 26° C., 27° C., 28° C., 29° C., 30° C., 31° C., 32° C., 33° C., or 34° C.).

Chemical Terms:

The term "acyl," as used herein, represents a hydrogen or an alkyl group (e.g., a haloalkyl group), as defined herein, that is attached to the parent molecular group through a carbonyl group, as defined herein, and is exemplified by formyl (i.e., a carboxyaldehyde group), acetyl, trifluoroacetyl, propionyl, butanoyl and the like. Exemplary unsubstituted acyl groups include from 1 to 7, from 1 to 11, or from 1 to 21 carbons. In some embodiments, the alkyl group is further substituted with 1, 2, 3, or 4 substituents as described herein.

The term "alkyl," as used herein, is inclusive of both straight chain and branched chain saturated groups from 1 to 20 carbons (e.g., from 1 to 10 or from 1 to 6), unless otherwise specified. Alkyl groups are exemplified by methyl, ethyl, n- and iso-propyl, n-, sec-, iso- and tert-butyl, neopentyl, and the like, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —NH$_2$) or a substituted amino (i.e., —N(R$^{N1}$)$_2$, where R$^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy, optionally substituted with an O-protecting group; (9) nitro; (10) oxo (e.g., carboxyaldehyde or acyl); (11) $C_{1-7}$ spirocyclyl; (12) thioalkoxy; (13) thiol; (14) —CO$_2$R$^{A'}$, optionally substituted with an O-protecting group and where R$^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CHO$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (15) —C(O)NR$^{B'}$R$^{C'}$, where each of R$^{B'}$ and R$^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —SO$_2$R$^{D'}$, where R$^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —SO$_2$NR$^{E'}$R$^{F'}$, where each of R$^{E'}$ and R$^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —C(O)R$^{G'}$, where R$^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) —$NR^{H1}C(O)R^{J1}$, wherein $R^{H1}$ is selected from the group consisting of (a1) hydrogen and (b1) $C_{1-6}$ alkyl, and $R^{J1}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) —$NR^{J1}C(O)OR^{K1}$, wherein $R^{J1}$ is selected from the group consisting of (a1) hydrogen and (b1) $C_{1-6}$ alkyl, and $R^{K1}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein. For example, the alkylene group of a $C_1$-alkaryl can be further substituted with an oxo group to afford the respective aryloyl substituent.

The term "alkylene" and the prefix "alk-," as used herein, represent a saturated divalent hydrocarbon group derived from a straight or branched chain saturated hydrocarbon by the removal of two hydrogen atoms, and is exemplified by methylene, ethylene, isopropylene, and the like. The term "$C_{x-y}$ alkylene" and the prefix "$C_{x-y}$ alk-" represent alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_{1-6}$, $C_{1-10}$, $C_{2-20}$, $C_{2-6}$, $C_{2-10}$, or $C_{2-20}$ alkylene). In some embodiments, the alkylene can be further substituted with 1, 2, 3, or 4 substituent groups as defined herein for an alkyl group.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, 2-butenyl, and the like. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, 1-propynyl, and the like. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

The term "amino," as used herein, represents —$N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkenyl, alkynyl, alkoxy, aryl, alkaryl, cycloalkyl, alkcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or alkheterocyclyl (e.g., alkheteroaryl), wherein each of these recited $R^{N1}$ groups can be optionally substituted, as defined herein for each group; or two $R^{N1}$ combine to form a heterocyclyl or an N-protecting group, and wherein each $R^{N2}$ is, independently, H, alkyl, or aryl. The amino groups of the invention can be an unsubstituted amino (i.e., —$NH_2$) or a substituted amino (i.e., —$N(R^{N1})_2$). In a preferred embodiment, amino is —$NH_2$ or —$NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each $R^{N2}$ can be H, $C_{1-20}$ alkyl (e.g., $C_{1-6}$ alkyl), or $C_{6-10}$ aryl.

The term "amino acid," as described herein, refers to a molecule having a side chain, an amino group, and an acid group (e.g., a carboxy group of —$CO_2H$ or a sulfo group of —$SO_3H$), wherein the amino acid is attached to the parent molecular group by the side chain, amino group, or acid group (e.g., the side chain). In some embodiments, the amino acid is attached to the parent molecular group by a carbonyl group, where the side chain or amino group is attached to the carbonyl group. Exemplary side chains include an optionally substituted alkyl, aryl, heterocyclyl, alkaryl, alkheterocyclyl, aminoalkyl, carbamoylalkyl, and carboxyalkyl. Exemplary amino acids include alanine, arginine, asparagine, aspartic acid, cysteine, glutamic acid, glutamine, glycine, histidine, hydroxynorvaline, isoleucine, leucine, lysine, methionine, norvaline, ornithine, phenylalanine, proline, pyrrolysine, selenocysteine, serine, taurine, threonine, tryptophan, tyrosine, and valine. Amino acid groups may be optionally substituted with one, two, three, or, in the case of amino acid groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —$NH_2$) or a substituted amino (i.e., —$N(R^{N1})_2$, where $R^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy; (9) nitro; (10) oxo (e.g., carboxyaldehyde or acyl); (11) $C_{1-7}$ spirocyclyl; (12) thioalkoxy; (13) thiol; (14) —$CO_2R^{A'}$, where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —$(CH_2)_{s2}$ $(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (15) —$C(O)NR^{B'}R^{C'}$, where each of $R^{B'}$ and $R^{C'}$ is, independently, selected from the group consisting of (a) hydrogen, (b) $C_{1-6}$ alkyl, (C) $C_{6-10}$ aryl, and (d) $C_{1-6}$ alk-$C_{6-10}$ aryl; (16) -$SO_2R^{D'}$, where $R^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —$SO_2NR^{E'}R^{F'}$, where each of $R^{E'}$ and $R^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —$C(O)R^{G'}$, where $R^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —$(CH_2)_{s2}$ $(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) —$NR^{H'}C(O)R^h$, wherein $R^{H'}$ is selected from the group consisting of (a1) hydrogen and (b1) $C_{1-6}$ alkyl, and $R^h$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) —$NR^{J'}C(O)OR^{K'}$, wherein $R^{J'}$ is selected from the group consisting of (a1) hydrogen and (b1) $C_{1-6}$ alkyl, and $R^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein.

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, anthracenyl, phenanthrenyl, fluorenyl, indanyl, indenyl, and the like, and may be optionally substituted with 1, 2, 3, 4, or 5 substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) alkyl, (b) $C_{6-10}$ aryl, and (c) alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) $C_{2-20}$ alkenyl; and (27) $C_{2-20}$ alkynyl. In some embodiments, each of these groups can be further substituted as described herein. For example, the alkylene group of a $C_1$-alkaryl or a $C_1$-alkheterocyclylcan be further substituted with an oxo group to afford the respective aryloyl and (heterocyclyl)oyl substituent group.

The term "arylalkyl," as used herein, represents an aryl group, as defined herein, attached to the parent molecular group through an alkylene group, as defined herein. Exemplary unsubstituted arylalkyl groups are from 7 to 30 carbons (e.g., from 7 to 16 or from 7 to 20 carbons, such as $C_{1-6}$ alk-$C_{6-10}$ aryl, $C_{1-10}$ alk-$C_{6-10}$ aryl, or $C_{1-20}$ alk-$C_{6-10}$ aryl). In some embodiments, the alkylene and the aryl each can be further substituted with 1, 2, 3, or 4 substituent groups as defined herein for the respective groups. Other groups preceded by the prefix "alk-" are defined in the same manner, where "alk" refers to a $C_{1-6}$ alkylene, unless otherwise noted, and the attached chemical structure is as defined herein.

The term "carbonyl," as used herein, represents a C(O) group, which can also be represented as C=O.

The term "carboxy," as used herein, means —$CO_2H$.

The term "cyano," as used herein, represents an —CN group.

The term "cycloalkyl," as used herein represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicycle heptyl, and the like. When the cycloalkyl group includes one carbon-carbon double bond or one carbon-carbon triple bond, the cycloalkyl group can be referred to as a "cycloalkenyl" or "cycloalkynyl" group respectively. Exemplary cycloalkenyl and cycloalkynyl groups include cyclopentenyl, cyclohexenyl, cyclohexynyl, and the like. The cycloalkyl groups of this invention can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{6-10}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) $C_{6-10}$ alkyl, (b) $C_{6-10}$ aryl, and (c) $C_{1-6}$ alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{6-10}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) oxo; (27) $C_{2-20}$ alkenyl; and (28) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "diastereomer," as used herein means stereoisomers that are not mirror images of one another and are non-superimposable on one another.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "halogen," as used herein, represents a halogen selected from bromine, chlorine, iodine, or fluorine.

The term "heteroalkyl," as used herein, refers to an alkyl group, as defined herein, in which one or two of the constituent carbon atoms have each been replaced by nitrogen, oxygen, or sulfur. In some embodiments, the heteroalkyl group can be further substituted with 1, 2, 3, or 4 substituent groups as described herein for alkyl groups. The terms "heteroalkenyl" and heteroalkynyl," as used herein refer to alkenyl and alkynyl groups, as defined herein, respectively, in which one or two of the constituent carbon atoms have each been replaced by nitrogen, oxygen, or sulfur. In some embodiments, the heteroalkenyl and heteroalkynyl groups can be further substituted with 1, 2, 3, or 4 substituent groups as described herein for alkyl groups.

The term "heteroaryl," as used herein, represents that subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

The term "heteroarylalkyl" refers to a heteroaryl group, as defined herein, attached to the parent molecular group through an alkylene group, as defined herein. Exemplary unsubstituted heteroarylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heteroaryl, $C_{1-10}$ alk-$C_{1-12}$ heteroaryl, or $C_{1-20}$ alk-$C_{1-12}$ heteroaryl). In some embodiments, the alkylene and the heteroaryl each can be further substituted with 1, 2, 3, or 4 substituent groups as defined herein for the respective group. Heteroarylalkyl groups are a subset of heterocyclylalkyl groups.

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, benzothienyl, and the like, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl); 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H -purinyl); 1,2,3,6-tetrahydro-2,6-dioxo-1H purinyl (e.g., 1,2,3,6-tetrahydro-3,7-dimethyl-2,6-dioxo-1H -purinyl); 2-oxobenz[c,d]indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl. Heterocyclic groups also include groups of the formula

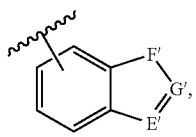

where

E' is selected from the group consisting of —N— and —CH—; F' is selected from the group consisting of —N=CH—, —NH—CH$_2$-, —NH—C(O)-, —NH—, —CH=N-, —CH$_2$—NH—, —C(O)-NH—, —CH=CH—, —CH$_2$—, —CH$_2$CH$_2$—, —CH$_2$O—, —OCH$_2$—, —O—, and —S—; and G' is selected from the group consisting of —CH— and —N—. Any of the heterocyclyl groups mentioned herein may be optionally substituted with one, two, three, four or five substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{2-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —(CH$_2$)$_q$CO$_2$R$^{A'}$, where q is an integer from zero to four, and R$^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —(CH$_2$)$_q$CONR$^{a}$R$^{C'}$, where q is an integer from zero to four and where R$^{B'}$ and R$^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —(CH$_2$)$_q$SO$_2$R$^{D'}$, where q is an integer from zero to four and where R$^{D'}$ is selected from the group consisting of (a) $C_{1-6}$ alkyl, (b) $C_{6-10}$ aryl, and (c) $C_{1-6}$ alk-$C_{6-10}$ aryl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) arylalkoxy; (25) $C_{1-6}$ alk-$C_{1-12}$ heterocyclyl (e.g., $C_{1-6}$ alk-$C_{1-12}$ heteroaryl); (26) oxo; (27) ($C_{1-12}$ heterocyclyl) imino; (28) $C_{2-20}$ alkenyl; and (29) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "hydrocarbon," as used herein, represents a group consisting only of carbon and hydrogen atoms.

The term "hydroxyl," as used herein, represents an —OH group. In some embodiments, the hydroxyl group can be substituted with 1, 2, 3, or 4 substituent groups (e.g., O-protecting groups) as defined herein for an alkyl.

The term "isomer," as used herein, means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "N-protected amino," as used herein, refers to an amino group, as defined herein, to which is attached one or two N-protecting groups, as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups, such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "O-protecting group," as used herein, represents those groups intended to protect an oxygen containing (e.g., phenol, hydroxyl, or carbonyl) group against undesirable reactions during synthetic procedures. Commonly used O-protecting groups are disclosed in Greene, "Protective Groups in Organic Synthesis," $3^{rd}$ Edition (John Wiley & Sons, New York, 1999), which is incorporated herein by reference. Exemplary O-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, a-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylphenoxyacetyl, dimethylformamidino, and 4-nitrobenzoyl; alkylcarbonyl groups, such as acyl, acetyl, propionyl, pivaloyl, and the like; optionally substituted arylcarbonyl groups, such as benzoyl; silyl groups, such as trimethylsilyl (TMS), tert-butyldimethylsilyl (TBDMS), tri-iso-propylsilyloxymethyl (TOM), triisopropylsilyl (TIPS), and the like; ether-forming groups with the hydroxyl, such methyl, methoxymethyl, tetrahydropyranyl, benzyl, p-methoxybenzyl, trityl, and the like; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, methyloxycarbonyl, and the like; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, 3-methyl-2-butenoxycarbonyl, and the like; haloalkoxycarbonyls, such as 2-chloroethoxycarbonyl, 2-chloroethoxycarbonyl, 2,2,2-trichloroethoxycarbonyl, and the like; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxycarbonyl, fluorenylmethyloxycarbonyl, and the like; and optionally substituted aryloxycarbonyl groups, such as phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, 2-chloro-4-nitrophenoxy-carbonyl, and the like); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenylmethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, 1,3-dioxolane, and the like; acylal groups; and dithiane groups, such as 1,3-dithianes, 1,3-dithiolane, and the like); carboxylic acid-protecting groups (e.g., ester groups, such as methyl ester, benzyl ester, t-butyl ester, orthoesters, and the like; and oxazoline groups.

The term "oxo" as used herein, represents =O.

The term "polyethylene glycol," as used herein, represents an alkoxy chain comprised of one or more momomer units, each monomer unit consisting of —OCH$_2$CH$_2$—. Polyethyelene glycol (PEG) is also sometimes referred to as polyethylene oxide (PEO) or polyoxyethylene (POE), and these terms may be considered interchangeable for the purpose of this invention. For example, a polyethylene glycol may have the structure, —(CH$_2$)$_{s2}$(OCH$_2$CH$_2$)$_{s1}$(CH$_2$)$_{s3}$O—, wherein s1 is an integer from 1 to 10 (e.g., from 1 to 6 or from 1 to 4), and each of s2 and s3, independently, is an integer from 0 to 10 (e.g., from 0 to 4, from 0 to 6, from 1 to 4, from 1 to 6, or from 1 to 10). Polyethylene glycol may also be considered to include an amino-polyethylene glycol of —NR$^{N1}$(CH$_2$)$_{s2}$(CH$_2$CH$_2$O)$_{s1}$(CH$_2$)$_{s3}$NR$^{N1}$_—, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted C$_{1-6}$ alkyl.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

The term "sulfonyl," as used herein, represents an —S(O)$_2$— group.

The term "thiol," as used herein represents an —SH group.

Definitions

As used herein, the term "administered in combination" or "combined administration" means that two or more agents are administered to a subject at the same time or within an interval such that there may be an overlap of an effect of each agent on the patient. In some embodiments, they are administered within 90 days (e.g., within 80, 70, 60, 50, 40, 30, 20, 10, 5, 4, 3, 2, or 1 day(s)), within 28 days (e.g., with 14, 7, 6, 5, 4, 3, 2, or 1 day(s), within 24 hours (e.g., 12, 6, 5, 4, 3, 2, or 1 hour(s), or within about 60, 30, 15, 10, 5, or 1 minute of one another. In some embodiments, the administrations of the agents are spaced sufficiently closely together such that a combinatorial (e.g., a synergistic) effect is achieved.

As used herein, "antibody" refers to a polypeptide whose amino acid sequence including immunoglobulins and fragments thereof which specifically bind to a designated antigen, or fragments thereof. Antibodies in accordance with the present invention may be of any type (e.g., IgA, IgD, IgE, IgG, or IgM) or subtype (e.g., IgA1, IgA2, IgG1, IgG2, IgG3, or IgG4). Those of ordinary skill in the art will appreciate that a characteristic sequence or portion of an antibody may include amino acids found in one or more regions of an antibody (e.g., variable region, hypervariable region, constant region, heavy chain, light chain, and combinations thereof). Moreover, those of ordinary skill in the art will appreciate that a characteristic sequence or portion of an antibody may include one or more polypeptide chains, and may include sequence elements found in the same polypeptide chain or in different polypeptide chains.

As used herein, "antigen-binding fragment" refers to a portion of an antibody that retains the binding characteristics of the parent antibody.

The terms "bifunctional chelate" or "bifunctional conjugate" as used interchangeably herein, refer to a compound that contains a chelating group or metal complex thereof, a linker group, and a therapeutic moiety, targeting moiety, or cross linking group.

The term "cancer" refers to any cancer caused by the proliferation of malignant neoplastic cells, such as tumors, neoplasms, carcinomas, sarcomas, leukemia's, and lymphomas. A "solid tumor cancer" is a cancer comprising an abnormal mass of tissue, e.g., sarcomas, carcinomas, and lymphomas. A "hematological cancer" or "liquid cancer," as used interchangeably herein, is a cancer present in a body fluid, e.g., lymphomas and leukemias.

The term "chelate" as used herein, refers to an organic compound or portion thereof that can be bonded to a central metal or radiometal atom at two or more points.

The term "conjugate," as used herein, refers to a molecule that contains a chelating group or metal complex thereof, a linker group, and which optionally contains a therapeutic moiety, targeting moiety, or cross linking group.

As used herein, the term "compound," is meant to include all stereoisomers, geometric isomers, and tautomers of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone—enol pairs, amide—imidic acid pairs, lactam—lactim pairs, amide—imidic acid pairs, enamine—imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl. Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional.

As used herein "detection agent" refers to a molecule or atom which is useful in diagnosing a disease by locating the cells containing the antigen. Various methods of labeling polypeptides with detection agents are known in the art. Examples of detection agents include, but are not limited to, radioisotopes and radionuclides, dyes (such as with the biotin-streptavidin complex), contrast agents, luminescent agents (e.g., FITC, rhodamine, lanthanide phosphors, cyanine, and near IR dyes), and magnetic agents, such as gadolinium chelates.

As used herein, the term "radionuclide," refers to an atom capable of undergoing radioactive decay (e.g. $^{3}H$, $^{14}C$, $^{15}N$, $^{18}F$, $^{35}S$, $^{47}Sc$, $^{55}Co$, $^{60}Cu$, $^{61}Cu$, $^{62}Cu$, $^{64}Cu$, $^{67}Cu$, $^{75}Br$, $^{76}Br$, $^{77}Br$, $^{89}Zr$, $^{86}Y$, $^{87}Y$, $^{90}Y$, $^{97}Ru$, $^{99}Tc$, $^{99m}Tc$, $^{105}Rh$, $^{109}Pd$, $^{111}In$, $^{123}I$, $^{124}I$, $^{125}I$, $^{131}I$, $^{149}Pm$, $^{149}Tb$, $^{153}Sm$, $^{166}Ho$, $^{177}Lu$, $^{186}Re$, $_{188}Re$, $^{198}Au$, $^{199}Au$, $^{203}Pb$, $^{211}At$, $^{212}Pb$, $^{212}Bi$, $^{213}Bi$, $^{223}Ra$, $^{225}Ac$, $^{227}Th$, $^{229Th}$, $^{66}Ga$, $^{67}Ga$, $^{68}Ga$, $^{82}Rb$, $^{117m}Sn$, $^{201}Tl$). The terms radioactive nuclide, radioisotope, or radioactive isotope may also be used to describe a radionuclide. Radionuclides may be used as detection agents, as described above. In some embodiments, the radionuclide may be an alpha-emitting radionuclide.

The term an "effective amount" of an agent (e.g., any of the foregoing conjugates), as used herein, is that amount sufficient to effect beneficial or desired results, such as clinical results, and, as such, an "effective amount" depends upon the context in which it is being applied.

The term "immunoconjugate," as used herein, refers to a conjugate that includes a targeting moiety, such as an antibody, nanobody, affibody, or a consensus sequence from a Fibronectin type III domain. In some embodiments, the immunoconjugate comprises an average of at least 0.10 conjugates per targeting moiety (e.g., an average of at least 0.2, 0.3, 0.4, 0.5, 0.6, 0.7, 0.8, 0.9, 1, 2, 3, 4, or 5 conjugates per targeting moiety).

The term "radioconjugate," as used herein, refers to any conjugate that includes a radioisotope or radionuclide, such as any of the radioisotopes or radionuclides described herein. In some embodiments the radioisotope or radionuclide is a metal chelate.

The term "radioimmunoconjugate," as used herein, refers to any immunoconjugate that includes a radioisotope or radionuclide, such as any of the radioisotopes or radionuclides described herein. In some embodiments the radioisotope or radionuclide is a metal chelate.

The term "radioimmunotherapy," as used herein, refers a method of using a radioimmunoconjugate to produce a therapeutic effect. In some embodiments, radioimmunotherapy may include administration of a radioimmunoconjugate to a subject in need thereof, wherein administration of the radioimmunoconjugate produces a therapeutic effect in the subject. In some embodiments, radioimmunotherapy may include administration of a radioimmunoconjugate to a cell, wherein administration of the radioimmunoconjugate kills the cell. Wherein radioimmunotherapy involves the selective killing of a cell, in some embodiments the cell is a cancer cell in a subject having cancer.

The term "pharmaceutical composition," as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, radioprotectants, sorbents, suspending or dispersing agents, sweeteners, or waters of hydration. Exemplary excipients include, but are not limited to: ascorbic acid, histidine, phosphate buffer, butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable salt," as use herein, represents those salts of the compounds described here that are, within the scope of sound medical judgment, suitable for use in contact with the tissues of humans and animals without undue toxicity, irritation, or allergic response. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, among others. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

The term "therapeutic moiety" as used herein refers to any molecule or any part of a molecule that confers a therapeutic benefit. In some embodiments, the therapeutic moiety is a protein or polypeptide, e.g., an antibody, an antigen-binding fragment thereof. In some embodiments, the therapeutic moiety is a small molecule.

The term "targeting moiety" as used herein refers to any molecule or any part of a molecule that binds to a given target. In some embodiments, the targeting moiety is a protein or polypeptide such as an antibody or antigen binding fragment thereof, a nanobody, an affibody, or consensus sequences from a Fibronectin type III domain.

The term "cross-linking group" as used herein refers to any reactive group that is able to join two or more molecules by a covalent bond. In some embodiments, the cross-linking group is an amino-reactive or thiol-reactive cross-linking group. In some embodiments, the amino-reactive or thiol-reactive cross-linking group comprises an activated ester such as a hydroxysuccinimide ester, 2,3,5,6-tetrafluorophenol ester, 4-nitrophenol ester or an imidate, anhydride, thiol, disulfide, maleimide, azide, alkyne, strained alkyne, strained alkene, halogen, sulfonate, haloacetyl, amine, hydrazide, diazirine, phosphine, tetrazine, isothiocyanate. In some embodiments, the cross linking group may by glycine-glycine-glycine and/or leucine-proline-(any amino acid)-threonine-glycine, which are the recognition sequences for coupling targeting agents with the linker using a sortase-mediated coupling reaction. The person having ordinary skill in the art will understand that the use of cross linking groups in the practice of the invention are not limited to the specific constructs disclosed herein, but rather may include other known cross linking groups.

The term "polypeptide" as used herein refers to a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides can include one or more "non-natural" amino acids or other entities that nonetheless are capable of integrating into a polypeptide chain. In some embodiments, a polypeptide may be glycosylated, e.g., a polypeptide may contain one or more covalently linked sugar moieties. In some embodiments, a single "polypeptide" (e.g., an antibody polypeptide) may comprise two or more individual polypeptide chains, which may in some cases be linked to one another, for example by one or more disulfide bonds or other means.

By "subject" is meant a human or non-human animal (e.g., a mammal).

By "substantial identity" or "substantially identical" is meant a polypeptide sequence that has the same polypeptide sequence, respectively, as a reference sequence, or has a specified percentage of amino acid residues, respectively, that are the same at the corresponding location within a reference sequence when the two sequences are optimally aligned. For example, an amino acid sequence that is "substantially identical" to a reference sequence has at least 50%, 60%, 70%, 75%, 80%, 85%, 90%, 95%, 96%, 97%, 98%, 99%, or 100% identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

As used herein, and as well understood in the art, "to treat" a condition or "treatment" of the condition (e.g., the conditions described herein such as cancer) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

DETAILED DESCRIPTION

Radiolabelled targeting moieties (also known as radioimmunoconjugates) are designed to target a protein or receptor that is upregulated in a disease state to deliver a radioactive payload to kill cells of interest (radioimmunotherapy). The process of delivering such a payload, via radioactive decay, produces the emission of an alpha, beta, or gamma particle or Auger electron that can cause direct effects to DNA (such as single or double stranded DNA breaks) or indirect effects such as by-stander or crossfire effects.

Radioimmunoconjugates typically contain a biological targeting moiety, a radioisotope, and a conjugate that links the two. Conjugates are formed when a bifunctional chelate is appended to the biological targeting molecule so that structural alterations to the compound are minimal while maintaining target affinity. Once radiolabelled, the final radioimmunoconjugate is formed.

Figure 1:
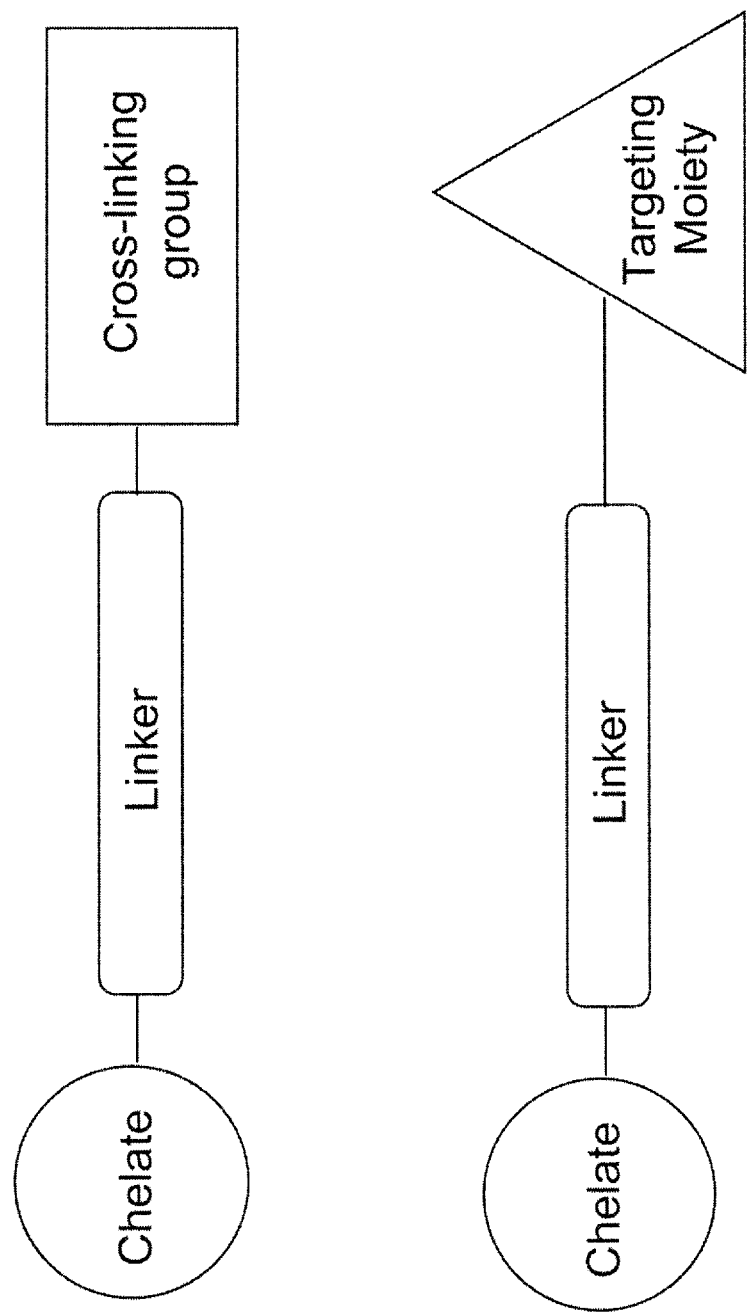
FIG. 1 is a schematic depicting the general structure of a conjugate comprising a chelate, a linker, and a cross-linking group (top) and a conjugate comprising a chelate, a linker, and a targeting moiety (bottom).

Bifunctional chelates structurally contain a chelate, the linker, and cross-linking group (FIG. 1). When developing new bifunctional chelates, most efforts focus around the chelating portion of the molecule. Several examples of bifunctional chelates have been described with various cyclic and acyclic structures that when conjugated to a targeted moiety. [Bioconjugate Chem. 2000, 11, 510-519, Bioconjugate Chem.2012, 23, 1029-1039, Mol Imaging Biol (2011) 13:215-221, Bioconjugate Chem.2002,13,110-115]

One the key factors of developing safe and effective radioimmunoconjugates is maximizing efficacy while minimizing off-target toxicity in normal tissue. While this statement is one of the core tenants of developing new drugs, the application to radioimmunotherapeutics presents new challenges. Radioimmunoconjugates do not need to block a receptor, as needed with a therapeutic antibody, or release the cytotoxic payload intracellularly, as required with an antibody drug conjugate, in order to have therapeutic efficacy. However, emission of the toxic particle is an event that occurs as a result of first-order (radioactive) decay and can occur at random anywhere inside the body after administration. Once the particle is released, damage could occur to surrounding cells within the range of the emission leading to the potential of off-target toxicity. Therefore, limiting exposure of these emissions to normal tissue is the key to developing new drugs [Bioconjugate Chem. 2006, 17, 1551-1560, Bioconjugate Chem. 2003, 14, 927-933].

One method potential method for reducing off-target exposure is to remove the radioactivity more effectively from the body. The most obvious mechanism is increase the rate of clearance of the biological targeting agent. This approach also likely requires identifying ways to shorten the half-life of the biological, which is a topic not well described for biological targeting agents. Regardless of the mechanism, increasing drug clearance will also negatively impact the pharmacodynamics/efficacy in that the more rapid removal of drug from the body will lower the effective concentration at the site of action, which, in turn, would require a higher total dose and would not achieve the desired results of reducing total radioactive dose to normal tissue.

Other efforts have focused on accelerating the metabolism of the portion of the molecule that contains the radioactive moiety. To this end, some efforts have been made to increase the rate of cleavage of the radioactivity from the biological targeting agents using what have been termed "cleavable linkers". Cleavable linkers, however, have been taken on different meaning as it relates to radioimmunoconjugates. Cornelissen, et al. has described cleavable linkers as those by which the bifunctional conjugate attaches to the biologic targeting agent through a reduced cysteine, whereas others have described the use of enzyme-cleavable systems that require the co-administration of the radioimmunoconjugate with a cleaving agent/enzyme to release [Mol Cancer Ther; 12(11) November 2013, Methods in Molecular Biology, 2009, 539, 191-211, Bioconjugate chemistry, Volume 14, Issue 5, p.927-33 (2003)]. These methods either change the nature of the biological targeting moiety, in the case of the cysteine linkage, or are not practical from a drug development perspective (enzyme cleavable systems) since, in the case of the citations provided, these methods require the administration of 2 agents.

The focus of the embodiments described herein centers on more effectively eliminating radioactivity from the body after catabolism and/or metabolism of the radioimmunoconjugate by making modifications to the linker region of the bifunctional chelate.

This is a novel approach since little information appears to exist describing the in vivo impact of the linker, especially as it applies to radioimmunoconjugates. One potential reason is that following catabolism/metabolism of the radioimmunoconjugate, one would expect the radiolabelled conjugate to undergo rapid systemic elimination. The supposition was furthered experimentally when the bifunctional chelate was administered alone; it cleared the bloodstream faster than the radioimmunoconjugate with that same bifunctional chelate. Based on this data, one would expect that following catabolism/metabolism of the radioimmunoconjugate, the metabolite containing the bifunctional chelate would also be rapidly eliminated.

However, rapid clearance of the metabolites containing the radiolabelled conjugate does not necessarily occur in vivo. Based on the results described below, the linker region of bifunctional chelates can directly impact the elimination of the radioactivity from the body following catabolism of the radioconjugate while not impacting the overall in vitro properties or the in vivo pharmacokinetics and pharmacodynamics of the radioimmunoconjugate. Data is presented below that demonstrates that the certain bifunctional chelates available commercially produce a slower rate and a lower extent of elimination of the total radioactivity from the body when compared to the embodiments described herein.

The excretion profiles of the embodiments described in the Examples represent unexpected findings. As previously reported, Quadri and Vriesendorp [Q. J. Nucl. Med. 1998, 42, 250-261], simple modifications to the linker region of the bifunctional chelate, regardless of their hydrophobicity, did not impact urinary excretion of the radioactivity. The results provided below clearly indicate that both hydrophobic and hydrophilic linkers can impact excretion patterns. In addition, the Examples below demonstrate that hepatobiliary clearance also plays a role in excretion.

Therefore, through the embodiments described herein, bifunctional chelates, when attached to biological targeting moieties, have been identified that achieve a reduction of total body radioactivity by increasing the extent of excretion of the catabolic/metabolic products while maintaining the pharmacokinetics of the intact molecule when compared to similar bifunctional chelates in the public domain. This reduction in total body radioactivity has been determined to be due to the clearance of catabolic/metabolic by-products and does not impact the other in vitro and in vivo properties such as degree of specificity (in vitro binding), cellular retention, and tumor uptake in vivo. When taken in whole, these embodiments achieve the desired properties of radioimmunoconjugates by reducing the body burden of radioactivity while maintaining on-target activity.

Therapeutic Moieties and Targeting Moieties

Therapeutic moieties include any molecule or any part of a molecule that confers a therapeutic benefit. In some embodiments, the therapeutic moiety is a protein or polypeptide, e.g., an antibody, an antigen-binding fragment thereof. In some embodiments, the therapeutic moiety is a small molecule. Targeting moieties include any molecule or any part of a molecule that binds to a given target. In some embodiments, the targeting moiety is a protein or polypeptide such as antibodies or antigen binding fragments thereof, nanobodies, affibodies, and consensus sequences from Fibronectin type III domains (e.g., Centyrins or Adnectins).

Polypeptides

Polypeptides include, for example, any of a variety of hematologic agents (including, for instance, erythropoietin, blood-clotting factors, etc.), interferons, colony stimulating factors, antibodies, enzymes, and hormones. The identity of a particular polypeptide is not intended to limit the present disclosure, and any polypeptide of interest can be a polypeptide in the present methods.

A reference polypeptide described herein can include a target-binding domain that binds to a target of interest (e.g., binds to an antigen). For example, a polypeptide, such as an antibody, can bind to a transmembrane polypeptide (e.g., receptor) or ligand (e.g., a growth factor). Exemplary molecular targets (e.g., antigens) for polypeptides described herein (e.g., antibodies) include CD proteins such as CD2, CD3, CD4, CD8, CD11, CD19, CD20, CD22, CD25, CD33, CD34, CD40, CD52; members of the ErbB receptor family such as the EGF receptor (EGFR, HER1, ErbB1), HER2 (ErbB2), HER3 (ErbB3) or HER4 (ErbB4) receptor; macrophage receptors such as CRIg; tumor necrosis factors such as TNFα or TRAIL/Apo-2; cell adhesion molecules such as LFA-1, Mac1, p150,95, VLA-4, ICAM-1, VCAM and avβ3 integrin including either α or β subunits thereof (e.g., anti-CD11a, anti-CD18 or anti-CD11b antibodies); growth factors and receptors such as EGF, FGFR (e.g., FGFR3) and VEGF; IgE; cytokines such as IL1; cytokine receptors such as IL2 receptor; blood group antigens; flk2/flt3 receptor; obesity (OB) receptor; mpl receptor; CTLA-4; protein C; neutropilins; ephrins and receptors; netrins and receptors; slit and receptors; chemokines and chemokine receptors such as CCL5, CCR4, CCR5; amyloid beta; complement factors, such as complement factor D; lipoproteins, such as oxidized LDL (oxLDL); lymphotoxins, such as lymphotoxin alpha (LTa). Other molecular targets include Tweak, B7RP-1, proprotein convertase subtilisin/kexin type 9 (PCSK9), sclerostin, c-kit, Tie-2, c-fms, and anti-M1.

Antibodies

An IgG antibody consists of two identical light polypeptide chains and two identical heavy polypeptide chains linked together by disulfide bonds. The first domain located at the amino terminus of each chain is variable in amino acid sequence, providing the antibody binding specificities found in each individual antibody. These are known as variable heavy (VH) and variable light (VL) regions. The other domains of each chain are relatively invariant in amino acid sequence and are known as constant heavy (CH) and constant light (CL) regions. For an IgG antibody, the light chain includes one variable region (VL) and one constant region (CL). An IgG heavy chain includes a variable region (VH), a first constant region (CH1), a hinge region, a second constant region (CH2), and a third constant region (CH3). In IgE and IgM antibodies, the heavy chain includes an additional constant region (CH4).

Antibodies described herein can include, for example, monoclonal antibodies, polyclonal antibodies, multispecific antibodies, human antibodies, humanized antibodies, camelid antibodies, chimeric antibodies, single-chain Fvs (scFv), disulfide-linked Fvs (sdFv), and anti-idiotypic (anti-Id) antibodies, and antigen-binding fragments of any of the above. Antibodies can be of any type (e.g., IgG, IgE, IgM, IgD, IgA and IgY), class (e.g., IgG1, IgG2, IgG3, IgG4, IgA1 and IgA2) or subclass.

The term "antigen binding fragment" of an antibody, as used herein, refers to one or more fragments of an antibody that retain the ability to specifically bind to an antigen. Examples of binding fragments encompassed within the term "antigen binding fragment" of an antibody include a Fab fragment, a F(ab')$_2$ fragment, a Fd fragment, a Fv fragment, a scFv fragment, a dAb fragment (Ward et al., (1989) Nature 341:544-546), and an isolated complementarity determining region (CDR). These antibody fragments can be obtained using conventional techniques known to those with skill in the art, and the fragments can be screened for utility in the same manner as are intact antibodies.

Antibodies or fragments described herein can be produced by any method known in the art for the synthesis of antibodies (see, e.g., Harlow et al., Antibodies: A Laboratory Manual, (Cold Spring Harbor Laboratory Press, 2nd ed. 1988); Brinkman et al., 1995, J. Immunol. Methods 182:41-50; WO 92/22324; WO 98/46645). Chimeric antibodies can be produced using the methods described in, e.g., Morrison, 1985, Science 229:1202, and humanized antibodies by methods described in, e.g., U.S. Pat. No. 6,180,370.

Additional antibodies described herein are bispecific antibodies and multivalent antibodies, as described in, e.g., Segal et al., J. Immunol. Methods 248:1-6 (2001); and Tutt et al., J. Immunol. 147: 60 (1991).

Insulin-Like Growth Factor 1 (IGF-1R) Antibodies

Insulin-like growth factor 1 receptor is a transmembrane protein found on the surface of human cells activated by insulin-like growth factor 1 (IGF-1) and 2 (IGF-2). IGF-1R is implicated in several cancers including breast cancer, non-small cell lung cancer, prostate cancer, colon cancer, sarcoma, and adrenocortical carcinoma, increased levels of IGF-1R are expressed on the surface of tumor cells of these cancers.

In some embodiments, the antibody, or an antigen-binding fragment thereof specifically binds insulin-like growth factor-1 receptor (IGF-1R).

Nanobodies

Nanobodies are antibody fragments consisting of a single monomeric variable antibody domain. Nanobodies may also be referred to as single-domain antibodies. Like antibodies, nanobodies bind selectively to a specific antigen. Nanobodies may be heavy-chain variable domains or light chain domains. Nanobodies may occur naturally or be the product of biological engineering. Nanobodies may be biologically engineered by site-directed mutagenesis or mutagenic screening (e.g., phage display, yeast display, bacterial display, mRNA display, ribosome display).

Affibodies

Affibodies are polypeptides or proteins engineered to bind to a specific antigen. As such, affibodies may be considered to mimic certain functions of antibodies. Affibodies may be engineered variants of the B-domain in the immunoglobulin-binding region of staphylococcal protein A. Affibodies may be engineered variants of the Z-domain, a B-domain that has lower affinity for the Fab region. Affibodies may be biologically engineered by site-directed mutagenesis or mutagenic screening (e.g., phage display, yeast display, bacterial display, mRNA display, ribosome display).

Affibody molecules showing specific binding to a variety of different proteins (e.g. insulin, fibrinogen, transferrin, tumor necrosis factor-a, IL-8, gp120, CD28, human serum albumin, IgA, IgE, IgM, HER2 and EGFR) have been generated, demonstrating affinities ($K_d$) in the pM to pM range.

Fibronectin Type III Domains

The Fibronectin type III domain is an evolutionarily conserved protein domain found in a wide-variety of extracellular proteins. The Fibronectin type III domain has been used as a molecular scaffold to produce molecules capable of selectively binding a specific antigen. Variants of the Fibronectin type III domains (FN3) that have been engineered for selective-binding may also be referred to as monobodies. FN3 domains may be biologically engineered by site-directed mutagenesis or mutagenic screening (e.g., CIS-display, phage display, yeast display, bacterial display, mRNA display, ribosome display).

Modified Polypeptides

The polypeptides of the invention may have a modified amino acid sequence. Modified polypeptides may be substantially identical to the corresponding reference polypeptide (e.g., the amino acid sequence of the modified polypeptide may have at least 50%, 60%, 70%, 75%, 80%, 85%, 90%, 95%, 96%, 97%, 98%, 99%, or 100% identity to the amino acid sequence of the reference polypeptide). In certain embodiments, the modification does not destroy significantly a desired biological activity. The modification may reduce (e.g., by at least 5%, 10%, 20%, 25%, 35%, 50%, 60%, 70%, 75%, 80%, 90%, or 95%), may have no effect, or may increase (e.g., by at least 5%, 10%, 25%, 50%, 100%, 200%, 500%, or 1000%) the biological activity of the original polypeptide. The modified polypeptide may have or may optimize a characteristic of a polypeptide, such as in vivo stability, bioavailability, toxicity, immunological activity, immunological identity, and conjugation properties.

Modifications include those by natural processes, such as post-translational processing, or by chemical modification techniques known in the art. Modifications may occur anywhere in a polypeptide including the polypeptide backbone, the amino acid side chains and the amino- or carboxy-terminus. The same type of modification may be present in the same or varying degrees at several sites in a given polypeptide, and a polypeptide may contain more than one type of modification. Polypeptides may be branched as a result of ubiquitination, and they may be cyclic, with or without branching. Cyclic, branched, and branched cyclic polypeptides may result from post-translational natural processes or may be made synthetically. Other modifications include pegylation, acetylation, acylation, addition of acetomidomethyl (Acm) group, ADP-ribosylation, alkylation, amidation, biotinylation, carbamoylation, carboxyethylation, esterification, covalent attachment to fiavin, covalent attachment to a heme moiety, covalent attachment of a nucleotide or nucleotide derivative, covalent attachment of drug, covalent attachment of a marker (e.g., fluorescent or radioactive), covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination.

A modified polypeptide can also include an amino acid insertion, deletion, or substitution, either conservative or non-conservative (e.g., D-amino acids, desamino acids) in the polypeptide sequence (e.g., where such changes do not substantially alter the biological activity of the polypeptide). In particular, the addition of one or more cysteine residues to the amino or carboxy terminus of any of the polypeptides of the invention can facilitate conjugation of these polypeptides by, e.g., disulfide bonding. For example, a polypeptide can be modified to include a single cysteine residue at the amino-terminus or a single cysteine residue at the carboxy-terminus. Amino acid substitutions can be conservative (i.e., wherein a residue is replaced by another of the same general type or group) or non-conservative (i.e., wherein a residue is replaced by an amino acid of another type). In addition, a naturally occurring amino acid can be substituted for a non-naturally occurring amino acid (i.e., non-naturally occurring conservative amino acid substitution or a non-naturally occurring non-conservative amino acid substitution).

Polypeptides made synthetically can include substitutions of amino acids not naturally encoded by DNA (e.g., non-naturally occurring or unnatural amino acid). Examples of non-naturally occurring amino acids include D-amino acids, N-protected amino acids, an amino acid having an acetylaminomethyl group attached to a sulfur atom of a cysteine, a pegylated amino acid, the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties.

Analogs may be generated by substitutional mutagenesis and retain the biological activity of the original polypeptide. Examples of substitutions identified as "conservative substitutions" are shown in Table 1. If such substitutions result in a change not desired, then other type of substitutions, denominated "exemplary substitutions" in Table 1, or as further described herein in reference to amino acid classes, are introduced and the products screened.

TABLE 1

Amino acid substitutions

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

Substantial modifications in function or immunological identity are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Cross-Linking Groups

A cross-linking group is a reactive group that is able to join two or more molecules by a covalent bond. Cross-linking groups may be used to attach the linker and chelating moiety to a therapeutic or targeting moiety. Cross-linking groups may also be used to attach the linker and chelating moiety to a target in vivo. In some embodiments, the cross-linking group is an amino-reactive or thiol-reactive cross-linking group, or a sortase-mediated coupling. In some embodiments, the amino-reactive, methionine reactive or thiol-reactive cross-linking group comprises an activated ester such as a hydroxysuccinimide ester, 2,3,5,6-tetrafluorophenol ester, 4-nitrophenol ester or an imidate, anhydride, thiol, disulfide, maleimide, azide, alkyne, strained alkyne, strained alkene, halogen, sulfonate, haloacetyl, amine, hydrazide, diazirine, phosphine, tetrazine, isothiocyanate, or oxaziridine.

In some embodiments, the sortase recognition sequence may comprise of a terminal glycine-glycine-glycine (GGG) and/or LPTXG (SEQ ID NO: 1) amino acid sequence, where X is any amino acid. The person having ordinary skill in the art will understand that the use of cross linking groups in the practice of the invention are not limited to the specific constructs disclosed herein, but rather may include other known cross linking groups.

Detection Agents

A detection agent is a molecule or atom which is administered conjugated to a polypeptide, e.g., an antibody or antigen-binding fragment thereof, and is useful in diagnosing a disease by locating the cells containing the antigen, radiation treatment planning, or treatment of a disease. Useful detection agents include, but are not limited to, radioisotopes, dyes (such as with the biotin-streptavidin complex), contrast agents, fluorescent compounds or molecules, luminescent agents, and enhancing agents (e.g., paramagnetic ions) for magnetic resonance imaging (MRI). In order to load a polypeptide component with a detection agent it may be necessary to react it with a reagent having a linker to which are attached the detection agent or multiple detection agents.

Radioisotopes and Radionuclides

Radioisotopes and radionuclides known in the art for their utility as detection agents include, but are not limited to, $^{3}$H, $^{14}$C, $^{15}$N, $^{18}$F, $^{35}$S, $^{47}$Sc, $^{55}$Co, $^{60}$Cu, $^{61}$Cu, $^{62}$Cu, $^{64}$Cu, $^{67}$Cu, $^{75}$Br, $^{76}$Br, $^{77}$Br, $^{89}$Zr, $^{86}$Y, $^{87}$Y, $^{90}$Y, $^{97}$Ru, $^{99}$Tc, $^{99m}$Tc, $^{105}$Rh, $^{109}$Pd, $^{111}$In, $^{123}$I, $^{124}$I, $^{125}$I, $^{131}$I, $^{149}$Pm, $^{149}$Tb, $^{153}$Sm, $^{166}$Ho, $^{177}$Lu, $^{186}$Re, $_{188}$Re, $^{198}$Au, $^{199}$Au, $^{203}$Pb, $^{211}$At, $^{212}$Pb, $^{212}$Bi, $^{213}$Bi, $^{223}$Ra, $^{225}$Ac, $^{227}$Th, $^{229Th}$, $^{66}$Ga, $^{67}$Ga, $^{68}$Ga, $^{82}$Rb, $^{117m}$Sn, $^{201}$Tl.

Chelating Moieties

Chelating moieties are known in the art for their utility as detection agents include, but are not limited to, DOTA (1,4,7,10-tetraazacyclododecane-1,4,7,10-tetraacetic acid), DOTMA (1R,4R,7R,10R)-α, α', α'', α'''-tetramethyl-1,4,7, 10-tetraazacyclododecane-1,4,7,10-tetraacetic acid, DOTAM (1,4,7,10-tetrakis(carbamoylmethyl)-1,4,7,10-tetraazacyclododecane), DOT PA (1,4,7,10-tetraazacyclododecane-1,4,7,10-tetra propionic acid), DO3AM-acetic acid (2-(4,7,10-tris(2-amino-2-oxoethyl)-1,4,7,10-tetraazacyclododecan-1-yl)acetic acid), DOTA-GA anhydride (2,2',2''-(10-(2,6-dioxotetrahydro-2H-pyran-3-yl)-1,4,7,10-tetraazacyclododecane-1,4,7-tril)triacetic acid, DOTP (1,4,7,10-tetraazacyclododecane-1,4,7,10-tetra (methylene phosphonic acid)), DOTMP (1,4,6,10-tetraazacyclodecane-1,4,7,10-tetramethylene phosphonic acid, DOTA-4AMP (1,4,7,10-tetraazacyclododecane-1,4,7,10-tetrakis(acetamido-methylenephosphonic acid), CB-TE2A (1,4,8,11-tetraazabicyclo[6.6.2]hexadecane-4,11-diacetic acid), NOTA (1,4,7-triazacyclononane-1,4,7-triacetic acid), NOTP (1,4,7-triazacyclononane-1,4,7-tri(methylene phosphonic acid), TETPA (1,4,8,11-tetraazacyclotetradecane-1, 4,8,11-tetrapropionic acid), TETA (1,4,8,11-tetraazacyclotetradecane-1,4,8,11-tetra acetic acid), HEHA (1,4,7,10,13, 16-hexaazacyclohexadecane-1,4,7,10,13,16-hexaacetic acid), PEPA (1,4,7,10,13-pentaazacyclopentadecane-N,N', N'',N''', N''''-pentaacetic acid), H$_4$octapa (N,N'-bis(6-carboxy-2-pyridylmethyl)-ethylenediamine-N,N'-diacetic acid), H$_2$dedpa (1,2-[[6-(carboxy)-pyridin-2-yl]-methylamino]ethane), H$_6$phospa (N,N'-(methylenephosphonate)-N,N'-[6-(methoxycarbonyl)pyridin-2-yl]-methyl-1,2-diaminoethane), TTHA (triethylenetetramine-N,N,N',N'',N''', N''''-hexaacetic acid), DO2P (tetraazacyclododecane dimethanephosphonic acid), HP-DO3A (hydroxypropyltetraazacyclododecanetriacetic acid), EDTA (ethylenediaminetetraacetic acid), Deferoxamine, DTPA (diethylenetriaminepentaacetic acid), DTPA-BMA (diethylenetriaminepentaacetic acid-bismethylamide), HOPO (octadentate hydroxypyridinones), or porphyrins. Chelating groups may be used in metal chelate combinations with metals, such as manganese, iron, and gadolinium and isotopes (e.g., isotopes in the general energy range of 60 to 4,000 keV), such as $_{47}$Sc, $^{55}$Co, $^{60}$Cu, $^{61}$Cu, $^{62}$Cu, $^{64}$Cu, $^{67}$Cu, $^{68}$Ga, $^{82}$Rb, $^{86}$Y, $^{87}$Y, $^{90}$Y, $^{97}$Ru, $^{99m}$Tc, $^{105}$Rh, $^{109}$Pd, $^{111}$In, $^{117m}$Sn, $^{149}$Tb, $^{149}$Pm, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, and $^{227}$Th.

Linkers

Linkers of the invention may have the structure of Formula I:

A-L$^1$-(L$^2$)$_n$-B      Formula I wherein A is chelating moiety or a metal complex thereof;
L$^1$ is optionally substituted C$_1$-C$_6$ alkyl, substituted C$_1$-C$_6$ heteroalkyl, substituted aryl or heteroaryl;
B is a is a therapeutic moiety, a targeting moiety, or cross-linking group,
or a pharmaceutically acceptable salt thereof;
n is 1-5;
each L$^2$, independently, has the structure:

(—X$^1$-L$^3$-Z$^1$—)      Formula II wherein is X$^1$ is C=O(NR$^1$), C=S(NR$^1$), OC=O(NR$^1$), NR$^1$C=O(O), NR$^1$C=O(NR$^1$), —CH$_2$PhC=O(NR$^1$), —CH$_2$Ph(NH)C=S(NR$^1$) , O, NR$^1$ and R$^1$ is H or optionally substituted C$_1$-C$_6$ alkyl or optionally substituted C$_1$-C$_6$ heteroalkyl, substituted aryl or heteroaryl;
L$^3$ is optionally substituted C$_1$-C$_{50}$ alkyl or optionally substituted C$_1$-C$_{50}$ heteroalkyl or C$_{5-20}$ polyethylene glycol;
Z$^1$ is CH$_2$, C=O, C=S, OC=O, NR$^1$C=O, NR$^1$ and R$^1$ is a hydrogen or optionally substituted C$_{1-6}$ alkyl, pyrrolidine-2,5-dione.

The conjugates of the invention comprise three distinct modules that together result in their increased effectiveness compared to those known in the art.

1. Chelating Moiety or Metal Complex Thereof:

Module A is included for incorporation of a detection agent (e.g., a chelating moiety or metal complex thereof). A metal complex may include an imaging radionuclide.

2. Linkers:

Linkers of the invention have the structure of Formula I:

A-L$^1$-(L$^2$)$_n$-B      Formula I wherein A is chelating moiety or a metal complex thereof;
L$^1$ is optionally substituted C$_1$-C$_6$ alkyl, substituted C$_1$-C$_6$ heteroalkyl, substituted aryl or heteroaryl;
B is a is a therapeutic moiety, a targeting moiety, or cross-linking group,
or a pharmaceutically acceptable salt thereof;
n is 1-5;
each L$^2$, independently, has the structure:

(—X$^1$-L$^3$-Z$^1$—)      Formula II wherein is X$^1$ is C=O(NR$^1$), C=S(NR$^1$), OC=O(NR$^1$), NR$^1$C=O(O), NR$^1$C=O(NR$^1$), —CH$_2$PhC=O(NR$^1$), —CH$_2$Ph(NH)C=S(NR$^1$), O, NR$^1$ and R$^1$ is H or optionally substituted C$_1$-C$_6$ alkyl or optionally substituted C$_1$-C$_6$ heteroalkyl, substituted aryl or heteroaryl;
L$^3$ is optionally substituted C$_1$-C$_{50}$ alkyl or optionally substituted C$_1$-C$_{50}$ heteroalkyl or C$_5$-C$_{20}$ polyethylene glycol;
Z$^1$ is CH$_2$, C=O, C=S, OC=O, NR$^1$C=O, NR$^1$ and R$^1$ is a hydrogen or optionally substituted C$_1$-C$_6$ alkyl, pyrrolidine-2,5-dione.

3. Therapeutic Moiety, Targeting Moiety, or Cross-Linking Group:

Module B is a therapeutic moiety (e.g., antibodies, antigen-binding fragments), a targeting moiety (e.g. nanobodies, affibodies, consensus sequences from Fibronectin type Ill domains), or a cross-linking group (e.g. amino-reactive, thiol-reactive cross-linking group, or a sortase-mediated coupling).

Administration and Dosage

The present invention also features pharmaceutical compositions that contain a therapeutically effective amount of a compound of the invention. The composition can be formulated for use in a variety of drug delivery systems. One or more physiologically acceptable excipients or carriers can also be included in the composition for proper formulation.

Suitable formulations for use in the present invention are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

The pharmaceutical compositions are intended for parenteral, intranasal, topical, oral, or local administration, such as by a transdermal means, for prophylactic and/or therapeutic treatment. The pharmaceutical compositions can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that include the above mention agents dissolved or suspended in an acceptable carrier, preferably an aqueous carrier, e.g., water, buffered water, saline, or PBS, among others. The compositions may contain pharmaceutically acceptable auxiliary substances as required to approximate physiological conditions, such as pH adjusting and buffering agents, tonicity adjusting agents, wetting agents, or detergents, among others. The invention also provides compositions for oral delivery, which may contain inert ingredients such as binders or fillers for the formulation of a unit dosage form, such as a tablet or a capsule. Furthermore, this invention provides compositions for local administration, which may contain inert ingredients such as solvents or emulsifiers for the formulation of a cream, an ointment, a gel, a paste, or an eye drop.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 6 and 7, such as 6 to 6.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The compositions containing an effective amount can be administered for radiation treatment planning, diagnostic, or therapeutic treatments. When administered for radiation treatment planning or diagnostic purposes, the conjugate is administered to a subject in a diagnostically effective dose and/or an amount effective to determine the therapeutically effective dose. In therapeutic applications, compositions are administered to a subject (e.g., a human) already suffering from a condition (e.g., cancer) in an amount sufficient to cure or at least partially arrest the symptoms of the disorder and its complications. An amount adequate to accomplish this purpose is defined as a "therapeutically effective amount," an amount of a compound sufficient to substantially improve at least one symptom associated with the disease or a medical condition. For example, in the treatment of cancer, an agent or compound that decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual. The conjugates of the invention can be used for the treatment of cancer by administering to a subject a first dose of any of the foregoing conjugates or compositions in an amount effective for radiation treatment planning, followed by administering a second dose of any of the foregoing conjugates or compositions in a therapeutically effective amount.

Amounts effective for these uses may depend on the severity of the disease or condition and the weight and general state of the subject. The therapeutically effective amount of the compositions of the invention and used in the methods of this invention applied to mammals (e.g., humans) can be determined by the ordinarily-skilled artisan with consideration of individual differences in age, weight, and the condition of the mammal. Because certain conjugates of the invention exhibit an enhanced ability to target cancer cells and residualize, the dosage of the compounds of the invention can be lower than (e.g., less than or equal to about 90%, 75%, 50%, 40%, 30%, 20%, 15%, 12%, 10%, 8%, 7%, 6%, 5%, 4%, 3%, 2%, 1%, 0.5%, or 0.1% of) the equivalent dose of required for a therapeutic effect of the unconjugated agent. The agents of the invention are administered to a subject (e.g., a mammal, such as a human) in an effective amount, which is an amount that produces a desirable result in a treated subject. Therapeutically effective amounts can also be determined empirically by those of skill in the art.

Single or multiple administrations of the compositions of the invention including an effective amount can be carried out with dose levels and pattern being selected by the treating physician. The dose and administration schedule can be determined and adjusted based on the severity of the disease or condition in the subject, which may be monitored throughout the course of treatment according to the methods commonly practiced by clinicians or those described herein.

The conjugates of the present invention may be used in combination with either conventional methods of treatment or therapy or may be used separately from conventional methods of treatment or therapy.

When the compounds of this invention are administered in combination therapies with other agents, they may be administered sequentially or concurrently to an individual. Alternatively, pharmaceutical compositions according to the present invention may be comprised of a combination of a compound of the present invention in association with a pharmaceutically acceptable excipient, as described herein, and another therapeutic or prophylactic agent known in the art.

By "antiproliferative" or "antiproliferative agent," as used interchangeably herein, is meant any anticancer agent, including those antiproliferative agents listed in Table 2, any of which can be used in combination with a conjugate of the invention to treat the medical conditions recited herein. Antiproliferative agents also include organo-platinum derivatives, naphtoquinone and benzoquinone derivatives, chrysophanic acid and anthroquinone derivatives thereof.

By "immunoregulatory agent" or "immunomodulatory agent," as used interchangeably herein, is meant any immuno-modulator, including those listed in Table 2, any of which can be used in combination with a conjugate of the invention to treat the medical conditions recited herein.

As used herein, "radiation sensitizer" includes any agent that increases the sensitivity of cancer cells to radiation therapy. Radiation sensitizers may include, but are not limited to, 5'fluorouracil, analogs of platinum (e.g., cisplatin, carboplatin, oxaliplatin), gemcitabine, EGFR antagonists (e.g., cetuximab, gefitinib), farnesyltransferase inhibitors, COX-2 inhibitors, bFGF antagonists, and VEGF antagonists.

TABLE 2

| | | |
|---|---|---|
| Alkylating agents | Busulfan | Chlorambucil |
| | dacarbazine | procarbazine |
| | ifosfamide | altretamine |
| | hexamethylmelamine | estramustine phosphate |
| | thiotepa | mechlorethamine |
| | dacarbazine | streptozocin |
| | lomustine | temozolomide |
| | cyclophosphamide | Semustine |
| Platinum agents | spiroplatin | lobaplatin (Aeterna) |
| | tetraplatin | satraplatin (Johnson Matthey) |
| | ormaplatin | BBR-3464 (Hoffmann-La Roche) |
| | iproplatin | SM-11355 (Sumitomo) |
| | picoplatin | AP-5280 (Access) |
| | oxaliplatin | cisplatin |
| | carboplatin | |
| Antimetabolites | azacytidine | trimetrexate |
| | Floxuridine | deoxycoformycin |
| | 2-chlorodeoxyadenosine | pentostatin |
| | 6-mercaptopurine | hydroxyurea |
| | 6-thioguanine | decitabine (SuperGen) |
| | cytarabine | clofarabine (Bioenvision) |
| | 2-fluorodeoxy cytidine | irofulven (MGI Pharma) |
| | methotrexate | DMDC (Hoffmann-La Roche) |
| | tomudex | ethynylcytidine (Taiho) |
| | fludarabine | gemcitabine |
| | raltitrexed | capecitabine |
| Topoisomerase inhibitors | amsacrine | exatecan mesylate (Daiichi) |
| | epirubicin | quinamed (ChemGenex) |
| | etoposide | gimatecan (Sigma-Tau) |
| | teniposide or mitoxantrone | diflomotecan (Beaufour-Ipsen) |
| | 7-ethyl-10-hydroxy-camptothecin | TAS-103 (Taiho) |
| | dexrazoxanet (TopoTarget) | elsamitrucin (Spectrum) |
| | pixantrone (Novuspharma) | J-107088 (Merck & Co) |
| | rebeccamycin analogue (Exelixis) | BNP-1350 (BioNumerik) |
| | BBR-3576 (Novuspharma) | CKD-602 (Chong Kun Dang) |
| | rubitecan (SuperGen) | KW-2170 (Kyowa Hakko) |
| | irinotecan (CPT-11) | hydroxycamptothecin (SN-38) |
| | topotecan | |
| Antitumor antibiotics | valrubicin | azonafide |
| | therarubicin | anthrapyrazole |
| | idarubicin | oxantrazole |
| | rubidazone | losoxantrone |
| | plicamycin | MEN-10755 (Menarini) |
| | porfiromycin | GPX-100 (Gem Pharmaceuticals) |
| | mitoxantrone (novantrone) | Epirubicin |
| | amonafide | mitoxantrone |
| | | doxorubicin |
| Antimitotic agents | colchicine | E7010 (Abbott) |
| | vinblastine | PG-TXL (Cell Therapeutics) |
| | vindesine | IDN 5109 (Bayer) |
| | dolastatin 10 (NCI) | A 105972 (Abbott) |
| | rhizoxin (Fujisawa) | A 204197 (Abbott) |
| | mivobulin (Warner-Lambert) | LU 223651 (BASF) |
| | cemadotin (BASF) | D 24851 (ASTAMedica) |
| | RPR 109881A (Aventis) | ER-86526 (Eisai) |
| | TXD 258 (Aventis) | combretastatin A4 (BMS) |
| | epothilone B (Novartis) | isohomohalichondrin-B (PharmaMar) |
| | T 900607 (Tularik) | ZD 6126 (AstraZeneca) |
| | T 138067 (Tularik) | AZ10992 (Asahi) |
| | cryptophycin 52 (Eli Lilly) | IDN-5109 (Indena) |
| | vinflunine (Fabre) | AVLB (Prescient NeuroPharma) |
| | auristatin PE (Teikoku Hormone) | azaepothilone B (BMS) |
| | BMS 247550 (BMS) | BNP-7787 (BioNumerik) |
| | BMS 184476 (BMS) | CA-4 prodrug (OXiGENE) |
| | BMS 188797 (BMS) | dolastatin-10 (NIH) |
| | taxoprexin (Protarga) | CA-4 (OXiGENE) |
| | SB 408075 (GlaxoSmithKline) | docetaxel |
| | Vinorelbine | vincristine |
| | Trichostatin A | paclitaxel |
| Aromatase inhibitors | aminoglutethimide | YM-511 (Yamanouchi) |
| | atamestane (BioMedicines) | formestane |
| | letrozole | exemestane |
| | anastrazole | |

TABLE 2-continued

| | | |
|---|---|---|
| Thymidylate synthase inhibitors | pemetrexed (Eli Lilly) ZD-9331 (BTG) | nolatrexed (Eximias) CoFactor ™ (BioKeys) |
| DNA antagonists | trabectedin (PharmaMar) glufosfamide (Baxter International) albumin + 32P (Isotope Solutions) thymectacin (NewBiotics) | edotreotide (Novartis) mafosfamide (Baxter International) apaziquone (Spectrum Pharmaceuticals) O6 benzyl guanine (Paligent) |
| Farnesyltransferase inhibitors | arglabin (NuOncology Labs) lonafarnib (Schering-Plough) BAY-43-9006 (Bayer) | tipifarnib (Johnson & Johnson) perillyl alcohol (DOR BioPharma) |
| Pump inhibitors | CBT-1 (CBA Pharma) tariquidar (Xenova) MS-209 (Schering AG) | zosuquidar trihydrochloride (Eli Lilly) biricodar dicitrate (Vertex) |
| Histone acetyltransferase inhibitors | tacedinaline (Pfizer) SAHA (Aton Pharma) MS-275 (Schering AG) | pivaloyloxymethyl butyrate (Titan) depsipeptide (Fujisawa) |
| Metalloproteinase inhibitors | Neovastat (Aeterna Laboratories) marimastat (British Biotech) | CMT-3 (CollaGenex) BMS-275291 (Celltech) |
| Ribonucleoside reductase inhibitors | gallium maltolate (Titan) triapine (Vion) | tezacitabine (Aventis) didox (Molecules for Health) |
| TNF alpha agonists/antagonists | virulizin (Lorus Therapeutics) CDC-394 (Celgene) | revimid (Celgene) |
| Endothelin A receptor antagonist | atrasentan (Abbott) ZD-4054 (AstraZeneca) | YM-598 (Yamanouchi) |
| Retinoic acid receptor agonists | fenretinide (Johnson & Johnson) LGD-1550 (Ligand) | alitretinoin (Ligand) |
| Immuno-modulators | interferon oncophage (Antigenics) GMK (Progenics) adenocarcinoma vaccine (Biomira) CTP-37 (AVI BioPharma) IRX-2 (Immuno-Rx) PEP-005 (Peplin Biotech) synchrovax vaccines (CTL Immuno) melanoma vaccine (CTL Immuno) p21 RAS vaccine (GemVax) MAGE-A3 (GSK) nivolumab (BMS) abatacept (BMS) pembrolizumab (Merck) | dexosome therapy (Anosys) pentrix (Australian Cancer Technology) ISF-154 (Tragen) cancer vaccine (Intercell) norelin (Biostar) BLP-25 (Biomira) MGV (Progenics) β-alethine (Dovetail) CLL therapy (Vasogen) Ipilimumab (BMS), CM-10 (cCam Biotherapeutics) atezolizumab (Genentech) |
| Hormonal and antihormonal agents | estrogens conjugated ethinyl estradiol chlortrianisen idenestrol hydroxyprogesterone medroxyprogesterone testosterone testosterone propionate; fluoxymesterone methyltestosterone diethylstilbestrol megestrol bicalutamide flutamide nilutamide | dexamethasone estrogens prednisone methylprednisolone prednisolone aminoglutethimide caproate leuprolide octreotide mitotane P-04 (Novogen) 2-methoxyestradiol (EntreMed) arzoxifene (Eli Lilly) tamoxifen toremofine goserelin Leuporelin bicalutamide |
| Photodynamic agents | talaporfin (Light Sciences) Theralux (Theratechnologies) motexafin gadolinium (Pharmacyclics) | Pd-bacteriopheophorbide (Yeda) lutetium texaphyrin (Pharmacyclics) hypericin |
| Kinase Inhibitors | imatinib (Novartis) leflunomide (Sugen/Pharmacia) ZD1839 (AstraZeneca) erlotinib (Oncogene Science) canertinib (Pfizer) squalamine (Genaera) SU5416 (Pharmacia) SU6668 (Pharmacia) ZD4190 (AstraZeneca) ZD6474 (AstraZeneca) vatalanib (Novartis) PKI166 (Novartis) GW2016 (GlaxoSmithKline) EKB-509 (Wyeth) trastuzumab (Genentech) OSI-774 (Tarceva ™) CI-1033 (Pfizer) SU11248 (Pharmacia) RH3 (York Medical) Genistein | EKB-569 (Wyeth) kahalide F (PharmaMar) CEP-701 (Cephalon) CEP-751 (Cephalon) MLN518 (Millenium) PKC412 (Novartis) Phenoxodiol (Novogen) C225 (ImClone) rhu-Mab (Genentech) MDX-H210 (Medarex) 2C4 (Genentech) MDX-447 (Medarex) ABX-EGF (Abgenix) IMC-1C11 (ImClone) Tyrphostins Gefitinib (Iressa) PTK787 (Novartis) EMD 72000 (Merck) Emodin Radicinol |

TABLE 2-continued

| | |
|---|---|
| | Radicinol |
| | Met-MAb (Roche) |
| SR-27897 (CCK A inhibitor, Sanofi-Synthelabo) | Vemurafenib (B-Raf enzyme inhibitor, Daiichi Sankyo) |
| tocladesine (cyclic AMP agonist, Ribapharm) | ceflatonin (apoptosis promotor, ChemGenex) |
| alvocidib (CDK inhibitor, Aventis) | BOX-1777 (PNP inhibitor, BioCryst) |
| CV-247 (COX-2 inhibitor, Ivy Medical) | ranpirnase (ribonuclease stimulant, Alfacell) |
| P54 (COX-2 inhibitor, Phytopharm) | galarubicin (RNA synthesis inhibitor, Dong-A) |
| CapCell ™ (CYP450 stimulant, Bavarian Nordic) | tirapazamine (reducing agent, SRI International) |
| GCS-100 (gal3 antagonist, GlycoGenesys) | N-acetylcysteine (reducing agent, Zambon) |
| G17DT immunogen (gastrin inhibitor, Aphton) | R-flurbiprofen (NF-kappaB inhibitor, Encore) |
| efaproxiral (oxygenator, Allos Therapeutics) | 3CPA (NF-kappaB inhibitor, Active Biotech) |
| PI-88 (heparanase inhibitor, Progen) | seocalcitol (vitamin D receptor agonist, Leo) |
| tesmilifene (histamine antagonist, YM BioSciences) | 131-I-TM-601 (DNA antagonist, TransMolecular) |
| histamine (histamine H2 receptor agonist, Maxim) | eflornithine (ODC inhibitor, ILEX Oncology) |
| tiazofurin (IMPDH inhibitor, Ribapharm) | minodronic acid (osteoclast inhibitor, Yamanouchi) |
| cilengitide (integrin antagonist, Merck KGaA) | |
| SR-31747 (IL-1 antagonist, Sanofi-Synthelabo) | indisulam (p53 stimulant, Eisai) |
| CCI-779 (mTOR kinase inhibitor, Wyeth) | aplidine (PPT inhibitor, PharmaMar) |
| exisulind (PDE V inhibitor, Cell Pathways) | gemtuzumab (CD33 antibody, Wyeth Ayerst) |
| CP-461 (PDE V inhibitor, Cell Pathways) | PG2 (hematopoiesis enhancer, Pharmagenesis) |
| AG-2037 (GART inhibitor, Pfizer) | |
| WX-UK1 (plasminogen activator inhibitor, Wilex) | Immunol ™ (triclosan oral rinse, Endo) |
| PBI-1402 (PMN stimulant, ProMetic LifeSciences) | triacetyluridine (uridine prodrug, Wellstat) |
| bortezomib (proteasome inhibitor, Millennium) | SN-4071 (sarcoma agent, Signature BioScience) |
| SRL-172 (T cell stimulant, SR Pharma) | |
| TLK-286 (glutathione S transferase inhibitor, Telik) | TransMID-107 ™ (immunotoxin, KS Biomedix) |
| | PCK-3145 (apoptosis promotor, Procyon) |
| PT-100 (growth factor agonist, Point Therapeutics) | doranidazole (apoptosis promotor, Pola) |
| | CHS-828 (cytotoxic agent, Leo) |
| midostaurin (PKC inhibitor, Novartis) | trans-retinoic acid (differentiator, NIH) |
| bryostatin-1 (PKC stimulant, GPC Biotech) | MX6 (apoptosis promotor, MAXIA) |
| CDA-II (apoptosis promotor, Everlife) | apomine (apoptosis promotor, ILEX Oncology) |
| SDX-101 (apoptosis promotor, Salmedix) | urocidin (apoptosis promotor, Bioniche) |
| rituximab (CD20 antibody, Genentech) | Ro-31-7453 (apoptosis promotor, La Roche) |
| carmustine | brostallicin (apoptosis promotor, Pharmacia) |
| Mitoxantrone | β-lapachone |
| Bleomycin | gelonin |
| Absinthin | cafestol |
| Chrysophanic acid | kahweol |
| Cesium oxides | caffeic acid |
| BRAF inhibitors, | Tyrphostin AG |
| PD-L1 inhibitors | PD-1 inhibitors |
| MEK inhibitors | CTLA-4 inhibitors |
| bevacizumab | sorafenib |
| angiogenesis inhibitors | |
| dabrafenib | |

The following Examples are intended to illustrate the synthesis of a representative number of conjugates and the use of these conjugates for the treatment of cancer. Accordingly, the Examples are intended to illustrate but not to limit the invention. Additional compounds not specifically exemplified may be synthesized using conventional methods in combination with the methods described herein.

EXAMPLES

Example 1

General Materials and Methods

The antibody used was HuMIgG (Aldrich, 14506). Lutetium-177 was received from Perkin Elmer as lutetium chloride in a 0.05 N hydrochloric acid solution.

Analytical HPLC-MS was performed using a Waters Acquity HPLC-MS system comprised of a Waters Acquity Binary Solvent Manager, a Waters Acquity Sample Manager (samples cooled to 10° C.), a Water Acquity Column Manager (column temperature 30° C.), a Waters Acquity Photodiode Array Detector (monitoring at 254 nm and 214 nm), a Waters Acquity TQD with electrosparay ionization and a Waters Acquity BEH C18, 2.1×50 (1.7 µm) column. Preparative HPLC was performed using a Waters HPLC system comprised of a Waters 1525 Binary HPLC pump, a Waters 2489 UV/Visible Detector (monitoring at 254 nm and 214 nm) and a Waters XBridge Prep phenyl or C18 19×100 mm (5 µm) column.

HPLC elution method 1: Waters Acquity BEH C18 2.1 ×50 mm (1.7 µm) column; mobile phase A: $H_2O$ (0.1% v/v TFA); mobile phase B: acetonitrile (0.1% v/v TFA); flow rate=0.3 mL/min; initial=90% A, 3-3.5 min=0% A, 4 min=90% A, 5 min=90% A.

HPLC elution method 2: Waters XBridge Prep Phenyl 19×100 mm (5 µm) column; mobile phase A: $H_2O$ (0.1% v/v TFA); mobile phase B: acetonitrile (0.1% v/v TFA); flow rate: 10 mL/min; initial=80% A, 13 min=0% A.

HPLC elution method 3: Waters Acquity BEH C18 2.1 ×50 mm (1.7 µm) column; mobile phase A: $H_2O$ (0.1% v/v TFA); mobile phase B: acetonitrile (0.1% v/v TFA); flow rate=0.3 mL/min; initial=90% A, 8 min=0% A, 10 min=0% A, 11 min=90% A, 12 min=90% A.

HPLC elution method 4: Waters XBridge Prep C18 OBD 19×100 mm (5 µm) column; mobile phase A: $H_2O$ (0.1% v/v TFA); mobile phase B: acetonitrile (0.1% v/v TFA); flow rate: 10 mL/min; initial=80% A, 3 min=80% A, 13 min=20% A, 18 min=0% A.

HPLC elution method 5: Waters XBridge Prep C18 OBD 19×100 mm (5 µm) column; mobile phase A: $H_2O$ (0.1% v/v TFA); mobile phase B: acetonitrile (0.1% v/v TFA); flow rate: 10 mL/min; initial=90% A, 3 min=90% A, 13 min=0% A, 20 min=0% A.

HPLC elution method 6: Waters XBridge Prep C18 OBD 19×100 mm (5 μm) column; mobile phase A: H$_2$O (0.1% v/v TFA); mobile phase B: acetonitrile (0.1% v/v TFA); flow rate: 10 mL/min; initial=75% A, 13 min=0% A, 15 min=0% A.

HPLC elution method 7: Waters XBridge Prep C18 OBD 19×100 mm (5 μm) column; mobile phase A: H$_2$O (0.1% v/v TFA); mobile phase B: acetonitrile (0.1% v/v TFA); flow rate: 10 mL/min; initial=80% A, 12 min=0% A, 15 min=0% A.

HPLC elution method 8: Waters XBridge Prep C18 OBD 19×100 mm (5 μm) column; mobile phase A: H$_2$O (0.1% v/v TFA); mobile phase B: acetonitrile (0.1% v/v TFA); flow rate: 10 mL/min; initial=90% A, 12 min=0% A, 15 min=0% A.

Analytical Size Exclusion Chromatography (SEC) was performed using a Waters system comprised of a Waters 1525 Binary HPLC pump, a Waters 2489 UV/Visible Detector (monitoring at 280 nm), a Bioscan Flow Count radiodetector (FC-3300) and TOSOH TSKgel G3000SWxl, 7.8× 300 mm column. The isocratic SEC method had a flow rate=1 mL/min, with a mobile phase of 0.1 M phosphate, 0.6M NaCl, 0.025% sodium azide, pH=7.

MALDI-MS (positive ion) performed using a MALDI Bruker Ultraflextreme Spectrometer.

Radio thin-layer chromatography (radioTLC) performed with Bioscan AR-2000 Imaging Scanner, carried out on iTLC-SG glass microfiber chromatography paper (Agilent Technologies, SGI0001) plates using citrate buffer (0.1 M, pH 5.5).

Example 2

Synthesis of 4-{[11-oxo-11-(2,3,5,6-tetrafluorophenoxy)undecyl]carbamoyl}-2-4,7,10-tris(carboxymethyl)-1,4,7,10-tetraazacyclododecan-1-yl]butanoic acid (Compound B)

Figure 2:
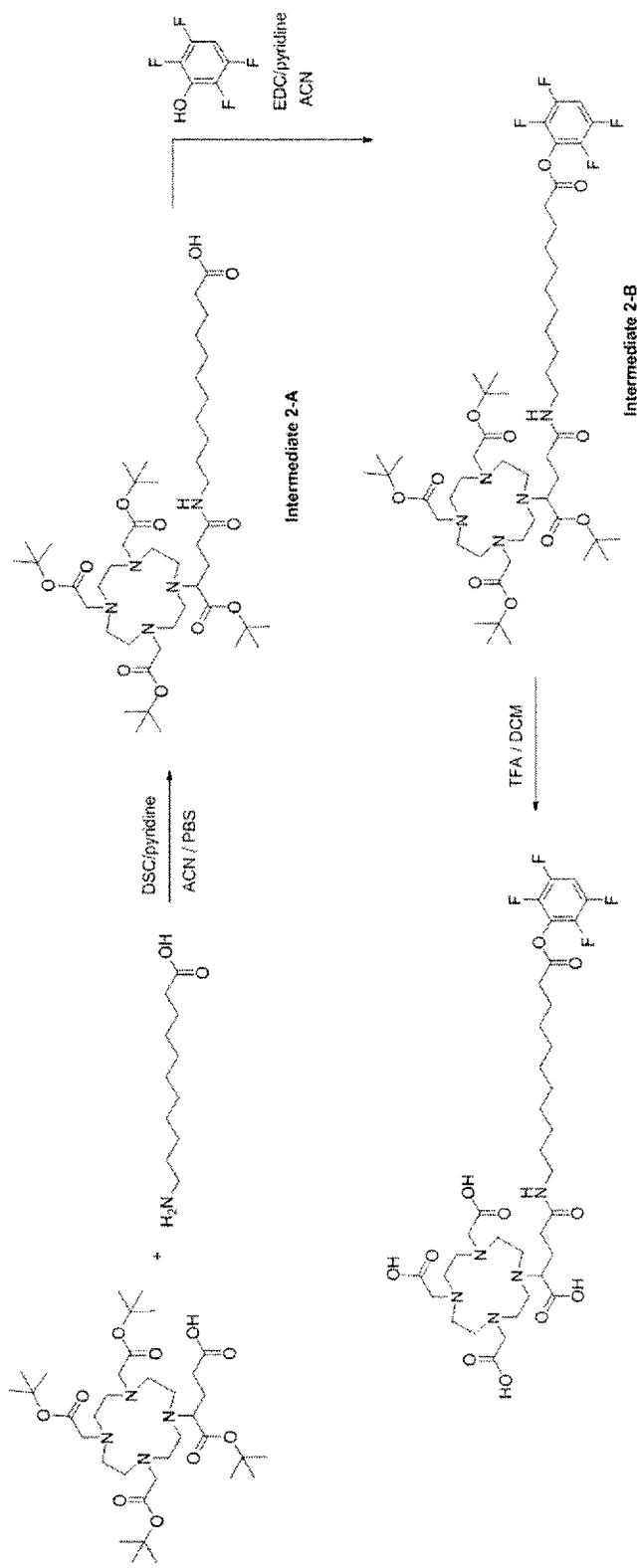
FIG. 2 is a schematic depicting the synthesis of the bifunctional chelate, 4-{[11-oxo-11-(2,3,5,6-tetrafluorophenoxy)undecyl]carbamoyl}-2-[4,7,10-tris(carboxymethyl)-1,4,7,10-tetraazacyclododecan-1-yl]butanoic acid (Compound B). The synthesis of Compound B is described in Example 3.

A bifunctional chelate, 4-{[11-oxo-11-(2,3,5,6-tetrafluorophenoxy)undecyl]carbamoyl}-2-[4,7,10-tris(carboxymethyl)-1,4,7,10-tetraazacyclododecan-1-yl]butanoic acid (Compound B), was synthesized according to the scheme provided in FIG. 2. To a solution of 5-(tert-butoxy)-5-oxo-4-(4,7,10-tris(2-(tert-butoxy)-2-oxoethyl)-1,4,7,10-tetraazacyclododecan-1-yl)pentanoic acid (DOTA-GA-(tBu)$_4$, 50 mg, 0.07 mmol) in ACN (2.0 mL) was added DSC (50 mg, 0.21 mmol) followed by pyridine (0.20 mL, 2.48 mmol). The reaction was stirred at room temperature for 1 h. To the reaction mixture was added 11-aminoundecanoic acid, (70 mg, 0.36 mmol) followed by PBS solution (1.0 mL) at room temperature. The reaction was stirred for 72 h at room temperature. The reaction mixture was filtered with syringe filter and purified directly by Prep-HPLC using method 6 to yield Intermediate 2-A (71 mg, 74.8%).

To a solution of Intermediate 2-A (40 mg , 0.03 mmol), TFP (90 mg , 0.54 mmol) and EDC (40 mg, 0.27 mmol) in ACN (1.0 mL) was added pyridine (0.05 mL , 50 mg , 0.62 mmol) at room temperature. The solution was stirred at room temperature for 24 h. The reaction was purified directly by Prep-HPLC using method 7 to provide Intermediate 2-B (33 mg, 82.5%) as a wax after concentration using a Biotage V10 Rapid Evaporator.

Intermediate 2-B (33 mg, 0.022 mmol) was dissolved DCM/TFA (1.0 mL/2.0 mL) and allowed to stir at room temperature for 24 h. The reaction was concentrated by air stream and purified directly by Prep-HPLC using method 8 to yield Compound B (14 mg, 50.0%) as a clear wax after concentration. An aliquot was analyzed by HPLC-MS elution method 3; retention time: 4.15 min; MS (positive ESI): found m/z 808.1 [M+H]$^+$; C$_{36}$H$_{54}$F$_4$N$_5$O$_{11}$ (calc. 808.8).

$^1$H NMR (600 MHz, DMSO-d$_6$) δ 7.99-7.88 (m, 1H), 7.82 (t, J=5.5 Hz, 1H), 3.78 (broad s, 4H), 3.43 (broad s, 12H), 3.08 (broad s, 4H), 3.00 (m, 3H), 2.93 (broad s, 3H), 2.77 (t, J=7.2 Hz, 2H), 2.30 (broad s, 2H), 1.88 (broad s, 2H), 1.66 (p, J=7.3 Hz, 2H), 1.36 (m, 4H), 1.32-1.20 (m, 9H).

Example 3

Synthesis of 4-{[2-(2-{2-[3-oxo-3-(2,3,5,6-tetrafluorophenoxy)propoxy]ethoxy}ethoxy)ethyl]carbamoyl}-2-[4,7,10-tris(carboxymethyl)-1,4,7,10-tetraazacyclododecan-1-yl]butanoic acid (Compound C)

Figure 3:
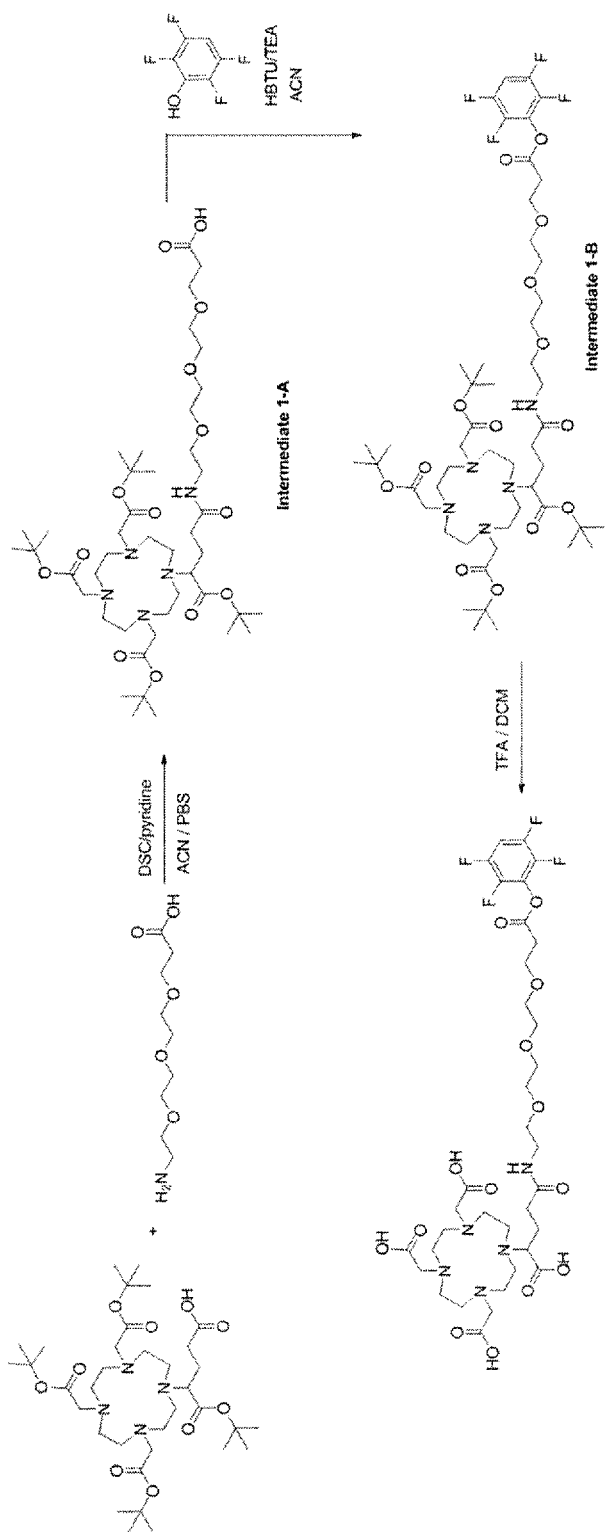
FIG. 3 is a schematic depicting the synthesis of the bifunctional chelate, 4-{[2-(2-{2-[3-oxo-3-(2,3,5,6-tetrafluorophenoxy)propoxy]ethoxy}ethoxy)ethyl]carbamoyl}-2-[4,7,10-tris(carboxymethyl)-1,4,7,10-tetraazacyclododecan-1-yl]butanoic acid (Compound C). The synthesis of Compound C is described in Example 4.

A bifunctional chelate, 4-{([2-(2-{2-[3-oxo-3-(2,3,5,6-tetrafluorophenoxy)propoxy]ethoxy}ethoxy)ethyl]carbamoyl}-2-[4,7,10-tris(carboxymethyl)-1,4,7,10-tetraazacyclododecan-1-yl]butanoic acid (Compound C), was synthesized according to the scheme provided in FIG. 3. To a solution of 5-(tert-butoxy)-5-oxo-4-(4,7,10-tris(2-(tert-butoxy)-2-oxoethyl)-1,4,7,10-tetraazacyclododecan-1-yl)pentanoic acid (DOTA-GA(tBu)$_4$, 100 mg, 0.143 mmol) in ACN (8.0 mL) was added DSC (73 mg, 0.285 mmol) and pyridine (0.80 mL, 9.89 mmol). The reaction mixture was stirred for 90 min at ambient temperature. This solution was added to a semi-solution of amino-PEG3-acid (63 mg, 0.285 mmol in 1.2 mL of DMF) in a 100 mL round bottom flask. After 4 hours at ambient temperature, the reaction was worked up by concentrating to dryness under a stream of air. The crude material was purified by HPLC elution method 2 (dissolved the crude in 6 mL of 20% ACN/H$_2$O). The fractions containing product were pooled and concentrated under vacuum and then co-evaporated with ACN (3×2 mL). Intermediate 1-A was obtained in 82% yield.

To vial containing Intermediate1-A (82 mg, 60 μmol) was added ACN (2 mL), NEt$_3$ (50 μL, 360 μmol, 6 equiv.), HBTU (23 mg, 60 μmol, 1 equiv) and a TFP solution (50 mg, 300 μmol, 5 equiv., dissolved in 250 μL of ACN). The resulting clear solution was stirred at ambient temperature for 3 h. The reaction was worked up by concentrating the solution to dryness under an air stream and was then diluted with ACN/H$_2$O (1:1, 3 mL total) and purified on preparative HPLC using elution method 4. The fractions containing product were pooled and concentrated under vacuum and then co-evaporated with ACN (3×2 mL). Intermediate 1-B was obtained as a clear residue (67 mg, 74% yield).

To a vial containing Intermediate 1-B (67 mg, 64 μmol) was added DCM (2 mL) and TFA (2 mL) and the resulting solution was stirred at ambient temperature for 16 h. Additional TFA (2 mL) was added and the reaction was stirred at ambient temperature for 6 h. The reaction was concentrated to dryness under an air stream with the crude product being finally dissolved in ACN/H$_2$O (1 mL of 10% ACN/H$_2$O). The crude reaction solution was then purified by preparative HPLC using elution method 5. The fractions containing product were pooled, frozen and lyophilized. Compound C was obtained as a white solid (36 mg, 63% yield). An aliquot was analyzed by HPLC-MS elution method 3; retention time: 3.11 min; MS (positive ESI): found m/z 828.4 [M+H]$^+$; C$_{34}$H$_{50}$F$_4$N$_5$O$_{14}$ (calc. 828.3).

$^1$H NMR (DMSO-d$_6$, 600 MHz) δ 7.97-7.91 (m, 2H), 3.77 (t, 2H, J=6.0 Hz), 3.58-3.55 (m, 2H), 3.53-3.48 (m, 8H), 3.44-3.38 (m, 10H), 3.23-3.08 (m, 11H), 3.02 (t, 2H, J=6.0 Hz), 2.93 (broad s, 4H), 2.30 (broad s, 2H), 1.87 (broad s, 2H).

Example 4

Synthesis of [$^{177}$Lu]-Compound A-Human-IgG

The compound Compound A (1.34 μmoles) was dissolved in sodium acetate buffer (20 μL, pH 6.5) and added to a solution containing the antibody Human-IgG antibody (6.7 nmoles) in a bicarbonate buffer (pH 8.5). After 45 minutes at ambient temperature the antibody conjugate product was purified via a HPLC SEC column (1 mL/min, eluted with acetate buffer (pH 6.5, 1 mM ascorbic acid). MALDI-TOF-MS (positive ion): Compound A-Human-IgG: found m/z 150360 [M+H]$^+$; Human-IgG: found m/z 148339 [M+H]$^+$.

As a typical reaction, Lu-177 (1.1 mCi, 5 μL) iswas added to a solution of Compound A-Human-IgG (90 μg in acetate buffer (pH 6.5) and ascorbic acid (1 μL, 0.1M in acetate buffer (pH 6.5)). The radiolabeling reaction was incubated at 37° C. for 90 minutes. The crude product, [$^{177}$Lu]-Compound A-Human-IgG, was purified via a Sephadex G-50 resin packed column eluted with acetate buffer (pH 6.5, 1 mM ascorbic acid. RadioTLC radiochemical purity: 98%; radiochemical yield: 45%; specific activity: 15.1 mCi/mg.

Example 5

Synthesis of [$^{177}$Lu]-Compound B-Human-IgG

The compound Compound B (1.17 μmoles) was dissolved in sodium acetate buffer (0.117 mL, pH 6.5). An aliquot of the Compound B solution (2 μL, 10 nmoles) was added to a solution containing the antibody Human-IgG (6.7 nmoles) in a bicarbonate buffer (pH 8.5). After 1 hour at ambient temperature the antibody conjugate product was purified via a Sephadex G-50 resin packed column. The antibody conjugate Compound A-Human-IgG was eluted from the column with acetate buffer (pH 6.5). MALDI-TOF-MS (positive ion): Compound B-Human-IgG found m/z 149949 [M+H]$^+$; Human-IgG found m/z 148540 [M+H]$^+$.

As a typical reaction, the Lu-177 (1.1 mCi, 5 μL) was added to a solution of Compound B-Human-IgG (100 μg in acetate buffer (pH 6.5) and ascorbic acid (1 μL, 0.1M in acetate buffer (pH 6.5)). The radiolabeling reaction was incubated at 37° C. for 30 minutes. The crude product, $^{177}$Lu-Compound B-Human-IgG, was purified via a HPLC SEC column (1 mL/min, eluted with acetate buffer (pH 6.5, 1 mM ascorbic acid) and concentrated by ultrafiltration (Vivaspin, 10 kDa,). RadioTLC radiochemical purity: 98%; radiochemical yield: 51%; specific activity: 9.68 mCi/mg.

Example 6

Synthesis of [$^{177}$Lu]-Compound C-Human-IgG

The compound Compound C (0.96 μmoles) was dissolved in sodium acetate buffer (95 μL, pH 6.5). An aliquot of the Compound C solution (2 μL, 20 nmoles) was added to a solution containing the antibody Human-IgG antibody (6.7 nmoles) in a bicarbonate buffer (pH 8.5). After 1 hour at ambient temperature the antibody conjugate product was purified via a Sephadex G-50 resin packed column. The antibody conjugate Compound C-Human-IgG was eluted from the column with acetate buffer (pH 6.5). MALDI-TOF-MS (positive ion): Compound C-Human-IgG: found m/z 150095 [M+H]$^+$; Human-IgG: found m/z 148540 [M+H]$^+$.

As a typical reaction, the Lu-177 (1.1 mCi, 5 μL) was added to a solution of Compound C-Human-IgG (100 μg in acetate buffer (pH 6.5) and ascorbic acid (1 μL, 0.1 M in acetate buffer (pH 6.5)). The radiolabeling reaction was incubated at 37° C. for 30 minutes. The crude product, [$^{177}$Lu]-Compound C-Human-IgG, was purified via a HPLC SEC column (1 mL/min, eluted with acetate buffer (pH 6.5, 1 mM ascorbic acid) and concentrated by ultrafiltration (Vivaspin, 10 kDa,). RadioTLC radiochemical purity: 98%; radiochemical yield: 37%; specific activity: 9.99 mCi/mg.

Example 7

Pharmacokinetic and Metabolism Studies of Human-IgG-Based Compounds

Groups of 4 or 5 mice (normal CD-1 or athymic CD-1 nude) were injected intravenously with approximately 15 microcuries of radiolabelled test compound. Test compounds with various linkers were synthesized and radiolabelled with lutetium-177. For pharmacokinetic studies, animals were sacrificed at specific time points, and blood and tumor (when applicable) were analyzed for total radioactivity. For metabolism studies, animals were placed in metabolic cages (4-5 per cage) for urine and feces collection every 24 hours for up to 7 days. The radioactive content of urine and feces samples was quantified and converted to total urine or feces output based on weight. Excretion profiles for urine, feces, or total excretion (urine+feces) were generated by plotting cumulative % injected dose (%ID) over time.

Non-targeted human IgG antibodies were used for metabolic excretion studies in order to demonstrate that the alterations in radioactivity excretion profiles directed by conjugation with linker Compound B and Compound C is a general process. The human IgG preparation used consisted of a purified mixture of all IgG isotypes (IgG1-4).

Figure 4:
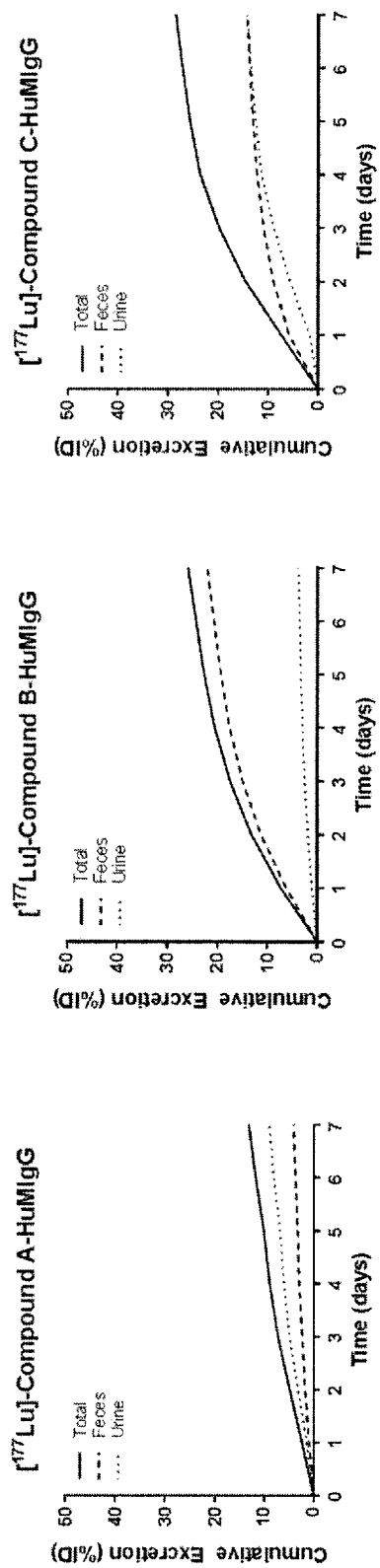
FIG. 4 is a series of graphs depicting the metabolic excretion profile of non-targeted human IgG antibody conjugates [$^{177}$Lu]-Compound B-HuMIgG, and [$^{177}$Lu]-Compound C-HuMIgG as compared to [$^{177}$Lu]-Compound A-HuMIgG, the methods and results of which are described in detail in Example 7.

The metabolic excretion profile of a non-targeted human IgG antibody conjugates [$^{177}$Lu]-Compound B-HuMIgG, and [$^{177}$Lu]-Compound C-HuMIgG were compared to [$^{177}$Lu]-Compound A-HuMIgG. The [$^{177}$Lu]-Compound A-HuMIgG was excreted slowly with just 13% of the injected dose (ID) eliminated over 7 days by low level urinary excretion. Compounds B and C directed distinctly different excretion routes and increased the amount total excretion of radioactivity over a 7 day period when compared to Compound A-HuMIgG. [$^{177}$Lu]-Compound B-HuMIgG was eliminated through the feces and [$^{177}$Lu]-Compound C-HuMIgG elimination was roughly equally divided between the urine and feces. Therefore, it was found that while the linker type impacted the route, rate, and extent of compound excretion (FIG. 4), it did not alter the overall blood pharmacokinetics of the total radioactivity associated with the radioimmunoconjugate. It was also observed that the improved excretion profile of the Compound B or Compound C when conjugated to antibodies is a general and reproducible effect.

Example 8

Synthesis of [$^{225}$Ac]-Compound A-Human-IgG

The compound Compound A (1.34 μmoles) was dissolved in sodium acetate buffer (20 μL, pH 6.5) and added to a solution containing the antibody Human-IgG antibody (6.7 nmoles) in a bicarbonate buffer (pH 8.5). After 45 minutes at ambient temperature the antibody conjugate product was purified via a HPLC SEC column (1 mL/min, eluted with acetate buffer (pH 6.5, 1 mM ascorbic acid). MALDI-TOF-MS (positive ion): Compound A-Human-IgG: found m/z 150360 [M+H]$^+$; Human-IgG: found m/z 148339 [M+H]$^+$.

As a typical reaction, Ac-225 (1.1 mCi, 5 μL) is added to a solution of Compound A-Human-IgG (90 μg in acetate buffer (pH 6.5) and ascorbic acid (1 μL, 0.1 M in acetate buffer (pH 6.5)). The radiolabeling reaction is incubated at ambient temperature (e.g., 20-25° C.) for 90 minutes. The crude product, [$^{225}$Ac]-Compound A-Human-IgG, is purified via a Sephadex G-50 resin packed column eluted with acetate buffer (pH 6.5, 1 mM ascorbic acid).

Example 9

Synthesis of [$^{225}$Ac]-Compound B-Human-IgG

The compound Compound B (1.17 μmoles) was dissolved in sodium acetate buffer (0.117 mL, pH 6.5). An aliquot of the Compound B solution (2 μL, 10 nmoles) was added to a solution containing the antibody Human-IgG (6.7 nmoles) in a bicarbonate buffer (pH 8.5). After 1 hour at ambient temperature the antibody conjugate product was purified via a Sephadex G-50 resin packed column. The antibody conjugate Compound A-Human-IgG was eluted from the column with acetate buffer (pH 6.5). MALDI-TOF-MS (positive ion): Compound B-Human-IgG found m/z 149949 [M+H]$^+$; Human-IgG found m/z 148540 [M+H]$^+$.

As a typical reaction, the Ac-225 (1.1 mCi, 5 μL) is added to a solution of Compound B-Human-IgG (100 μg in acetate buffer (pH 6.5) and ascorbic acid (1 μL, 0.1 M in acetate buffer (pH 6.5)). The radiolabeling reaction is incubated at ambient temperature (e.g., 20-25° C.) for 30 minutes. The crude product, [$^{225}$Ac]-Compound B-Human-IgG, is purified via a HPLC SEC column (1 mL/min, eluted with acetate buffer (pH 6.5, 1 mM ascorbic acid) and concentrated by ultrafiltration (Vivaspin, 10 kDa).

Example 10

Synthesis of [$^{225}$Ac]-Compound C-Human-IgG

The compound Compound C (0.96 μmoles) was dissolved in sodium acetate buffer (95 μL, pH 6.5). An aliquot of the Compound C solution (2 μL, 20 nmoles) was added to a solution containing the antibody Human-IgG antibody (6.7 nmoles) in a bicarbonate buffer (pH 8.5). After 1 hour at ambient temperature the antibody conjugate product was purified via a Sephadex G-50 resin packed column. The antibody conjugate Compound C-Human-IgG was eluted from the column with acetate buffer (pH 6.5). MALDI-TOF-MS (positive ion): Compound C-Human-IgG: found m/z 150095 [M+H]$^+$; Human-IgG: found m/z 148540 [M+H]$^+$.

As a typical reaction, the Ac-225 (1.1 mCi, 5 μL) is added to a solution of Compound C-Human-IgG (100 μg in acetate buffer (pH 6.5) and ascorbic acid (1 μL, 0.1 M in acetate buffer (pH 6.5)). The radiolabeling reaction is incubated at ambient temperature (e.g., 20-25° C.) for 30 minutes. The crude product, [$^{225}$Ac]-Compound C-Human-IgG, is purified via a HPLC SEC column (1 mL/min, eluted with acetate buffer (pH 6.5, 1 mM ascorbic acid) and concentrated by ultrafiltration (Vivaspin, 10 kDa,).

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features herein before set forth.

What is claimed is:

1. A compound having the structure of Formula I below, or a pharmaceutically acceptable salt thereof:

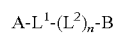   Formula I wherein
 A is a chelating moiety or a metal complex thereof,
  wherein said chelating moiety is selected from the group consisting of DOTA (1,4,7,10-tetraazacyclododecane-1,4,7,10-tetraacetic acid), DOTMA (1R,4R,7R,10R)-α,α',α'',α'''-tetramethyl-1,4,7,10-tetraazacyclododecane-1,4,7,10-tetraacetic acid, DOTAM (1,4,7,10-tetrakis(carbamoylmethyl)-1,4,7,10-tetraazacyclododecane), DO3AM-acetic acid (2-(4,7,10-tris(2-amino-2-oxoethyl)-1,4,7,10-tetraazacyclododecan-1-yl)acetic acid), DOTP (1,4,7,10-tetraazacyclododecane-1,4,7,10-tetra(methylene phosphonic acid)), DOTA-4AMP (1,4,7,10-tetraazacyclododecane-1,4,7,10-tetrakis(acetamido-methylenephosphonic acid), NOTA (1,4,7-triazacyclononane-1,4,7-triacetic acid), and HP-DO3A (hydroxypropyltetraazacyclododecanetriacetic acid),
 wherein the metal of said metal complex is selected from the group consisting of Bi, Pb, Y, Mn, Cr, Fe, Co, Zn, Ni, Tc, In, Ga, Cu, Re, a lanthanide, an actinide, or
 the metal of said metal complex is a radionuclide selected from the group consisting of $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{89}$Zr, $^{90}$Y, $^{97}$Ru, $^{99}$Tc, $^{99m}$Tc, $^{105}$Rh, $^{109}$Pd, $^{111}$In, $^{117m}$Sn, $^{149}$Pm, $^{149}$Tb, $^{153}$Sm, $^{166}$Ho, $^{177}$Lu, $^{186}$Re, $^{188}$Re, $^{198}$Au, $^{199}$Au, $^{201}$Tl, $^{203}$Pb, $^{211}$At, $^{212}$Pb, $^{212}$Bi, $^{213}$Bi, $^{23}$Ra, $^{225}$Ac, $^{227}$Th, and $^{229}$Th;

L¹ is optionally substituted $C_1$-$C_6$ alkyl or optionally substituted $C_1$-$C_6$ heteroalkyl;

B is a human or humanized IgG antibody or an antigen-binding fragment thereof;

n is 1; and

L² has the structure:

(—X¹-L³-Z¹—)     Formula II wherein X¹ is C=O(NR¹) or NR¹, in which R¹ is H or optionally substituted $C_1$-$C_6$ alkyl or optionally substituted $C_1$-$C_6$ heteroalkyl, substituted aryl or heteroaryl;

L³ is optionally substituted $C_1$-$C_{50}$ alkyl or optionally substituted $C1$-$C_{50}$ heteroalkyl; and Z¹ is $CH_2$, C=O, C=S, OC=O, $NR^1$C=O, NR¹; in which R¹ is hydrogen, optionally substituted $C_1$-$C_6$ alkyl, or pyrrolidine-2,5-dione.

2. The compound in claim 1, wherein the chelating moiety is DOTA (1,4,7,10-tetraazacyclododecane-1,4,7,10-tetraacetic acid).

3. The compound of claim 2, wherein the chelating moiety has the structure:

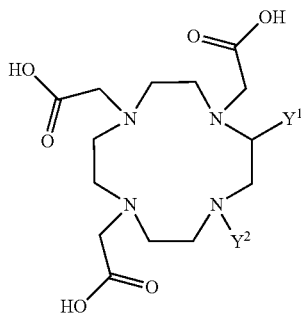

Wherein Y¹ is —$CH_2OCH_2(L^2)_n$—B, C=O($L^2)_n$—B, or C=S($L^2)_n$—B and Y² is —$CH_2CO_2H$; or Y¹ is H and Y² is L¹—$(L^2)_n$—B.

4. The compound of claim 1, wherein L¹ has the structure:

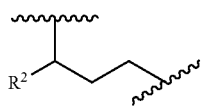

Formula III wherein R² is hydrogen or —$CO_2H$.

5. The compound of claim 4, wherein A is a metal complex and the metal of said metal complex is a radionuclide selected from the group consisting of ⁶⁴Cu, ⁶⁸Ga, ⁹⁰Y, ¹¹¹In, ¹⁷⁷Lu, ²²⁵Ac, and ²²⁷Th, wherein the metal is for use in imaging or therapeutic agents.

6. The compound of claim 3, wherein Y¹ is H.

7. The compound of claim 1, wherein X¹ is C=O(NR¹) and R¹ is H.

8. The compound of claim 1, wherein Z¹ is —$CH_2$.

9. The compound of claim 1, wherein the compound is selected from the group consisting of:

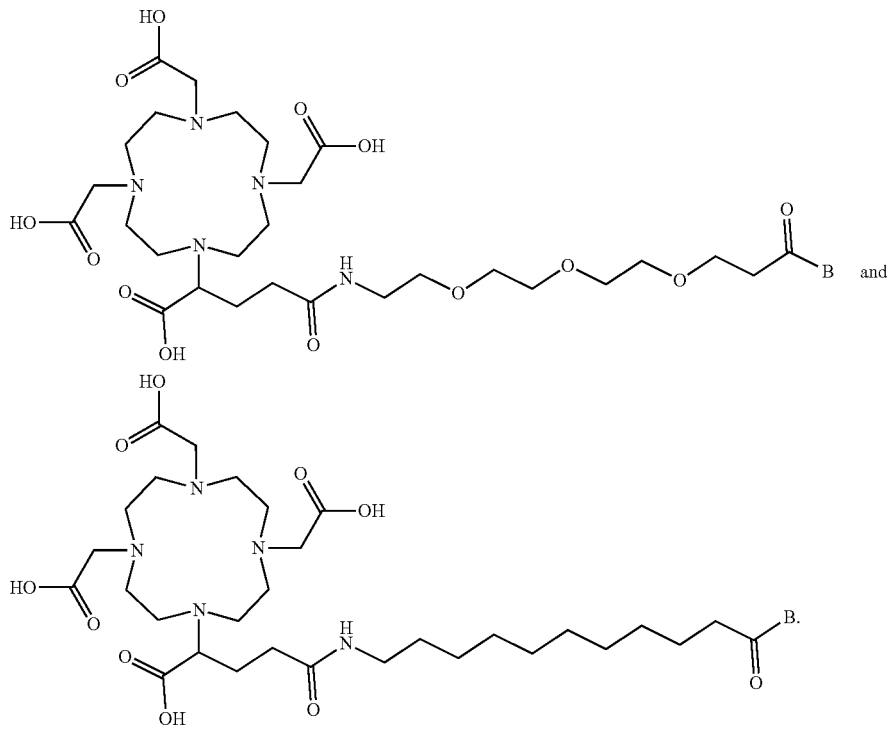

10. The compound of claim 5, wherein the radionuclide is $^{68}$Ga, $^{111}$In, $^{177}$Lu, or $^{225}$Ac.

11. The compound of claim 10, wherein the radionuclide is $^{111}$In.

12. The compound of claim 10, wherein the radionuclide is $^{68}$Ga.

13. The compound of claim 1, wherein the metal is an alpha-emitting radionuclide.

14. The compound of claim 13, wherein the radionuclide is $^{225}$Ac or a progeny thereof.

15. A pharmaceutical composition comprising a compound of claim 1 and a pharmaceutically acceptable excipient.

16. The compound of claim 1, wherein $L^3$ is $C_5$-$C_{20}$ polyethylene glycol.

* * * * *

UNITED STATES PATENT AND TRADEMARK OFFICE
CERTIFICATE OF CORRECTION

PATENT NO. : 11,191,854 B2
APPLICATION NO. : 15/971963
DATED : December 7, 2021
INVENTOR(S) : Eric Steven Burak et al.

It is certified that error appears in the above-identified patent and that said Letters Patent is hereby corrected as shown below:

In the Claims

In Claim 1, Column 44, Line 67, replace "$^{23}$Ra," with --$^{223}$Ra--.

In Claim 1, Column 45, Line 13, replace "OC=O, NR$^1$C=O, NR$^1$;" with --OC=O, NR$^1$C=O, or NR$^1$,--.

Signed and Sealed this
Twenty-ninth Day of November, 2022

Katherine Kelly Vidal
*Director of the United States Patent and Trademark Office*

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Sortase recognition sequence may comprise this
      sequence.
<220> FEATURE:
<221> NAME/KEY: VARIANT
<222> LOCATION: (4)..(4)
<223> OTHER INFORMATION: Any amino acid

<400> SEQUENCE: 1

Leu Pro Thr Xaa Gly
1               5
```